United States Patent
Krayer et al.

(10) Patent No.: US 10,665,348 B1
(45) Date of Patent: May 26, 2020

(54) RISK ASSESSMENT AND EVENT DETECTION

(71) Applicant: C/HCA, Inc., Nashville, TN (US)

(72) Inventors: Christian Krayer, Nolensville, TN (US); William Michael Gregg, Nashville, TN (US); Thomas Andrew Doyle, Franklin, TN (US); Paul Brient, Wayland, MA (US); Christopher Wobensmith, Nashville, TN (US); Jim Najib Jirjis, Nashville, TN (US); Victoria Weaver, Mt. Juliet, TN (US); Jonathan Perlin, Nashville, TN (US); Paul Martin Paslick, Nashville, TN (US); Edmund Jackson, Nashville, TN (US); Sarah Hume Buta, Arlington, MA (US); Erin S. Jospe, Newton, MA (US); Umesh P. Phirke, Newton, MA (US)

(73) Assignee: C/HCA, Inc., Denver, CO (US)

( * ) Notice: Subject to any disclaimer, the term of this patent is extended or adjusted under 35 U.S.C. 154(b) by 855 days.

(21) Appl. No.: 15/156,503

(22) Filed: May 17, 2016

Related U.S. Application Data

(60) Provisional application No. 62/163,220, filed on May 18, 2015, provisional application No. 62/317,844, filed on Apr. 4, 2016.

(51) Int. Cl.
*G16H 10/60* (2018.01)
*G16H 50/30* (2018.01)
*G16H 40/20* (2018.01)

(52) U.S. Cl.
CPC ............. *G16H 50/30* (2018.01); *G16H 10/60* (2018.01); *G16H 40/20* (2018.01)

(58) Field of Classification Search
CPC ........ G16H 10/60; G16H 50/20; G16H 40/20; G06Q 50/24; G06Q 10/06
See application file for complete search history.

(56) References Cited

U.S. PATENT DOCUMENTS

| | | | |
|---|---|---|---|
| 6,629,937 | B2 | 10/2003 | Watrous |
| 7,769,600 | B2 | 8/2010 | Iliff |
| 8,094,009 | B2 | 1/2012 | Allen |
| 8,271,471 | B1 | 9/2012 | Kamvar |
| 9,060,683 | B2 | 6/2015 | Tran |

(Continued)

OTHER PUBLICATIONS

U.S. Appl. No. 15/684,747, filed Aug. 23, 2017, Notice of Allowance dated Oct. 19, 2017, all pages.

(Continued)

*Primary Examiner* — Christopher L Gilligan
*Assistant Examiner* — Christine Y Liao
(74) *Attorney, Agent, or Firm* — Kilpatrick Townsend & Stockton, LLP

(57) ABSTRACT

In some examples, structured and unstructured data is analyzed to determine whether a user is at risk for a certain condition. The results of this analysis can be included in a risk assessment. In some examples, structured and unstructured data is analyzed to determine whether a particular event has taken place. Once detection of occurrence of the event has taken place, a notification is generated that a correct recipient is identified. In addition, it is determined if and how the notification should be escalated.

20 Claims, 26 Drawing Sheets

(56) References Cited

U.S. PATENT DOCUMENTS

| | | | |
|---|---|---|---|
| 9,081,879 B2 | 7/2015 | Iliff | |
| 9,269,116 B2 | 2/2016 | Bulat | |
| 9,524,569 B2 * | 12/2016 | Moore | G16H 10/60 |
| 9,779,611 B1 | 10/2017 | Krayer et al. | |
| 2001/0042119 A1 | 11/2001 | Urano | |
| 2004/0172222 A1 | 9/2004 | Simpson | |
| 2005/0075970 A1 | 4/2005 | Doyle | |
| 2005/0288965 A1 | 12/2005 | Eaton et al. | |
| 2006/0111941 A1 | 5/2006 | Blom | |
| 2006/0241978 A1 | 10/2006 | Yoshii | |
| 2007/0094046 A1 * | 4/2007 | Cobbs | G16H 40/20 705/2 |
| 2007/0185390 A1 | 8/2007 | Perkins | |
| 2007/0250345 A1 | 10/2007 | Walker | |
| 2008/0091464 A1 | 4/2008 | Lipscher | |
| 2008/0270189 A1 | 10/2008 | Howard | |
| 2010/0094649 A1 | 4/2010 | White | |
| 2011/0046979 A1 | 2/2011 | Tulipano et al. | |
| 2012/0101847 A1 | 4/2012 | Johnson | |
| 2012/0109683 A1 | 5/2012 | Ebadollahi et al. | |
| 2012/0117476 A1 * | 5/2012 | Siegrist | G16H 40/20 715/733 |
| 2012/0130734 A1 | 5/2012 | White | |
| 2012/0224057 A1 | 9/2012 | Gill | |
| 2014/0067418 A1 | 3/2014 | Hyzy | |
| 2014/0188895 A1 | 7/2014 | Wang et al. | |
| 2014/0316813 A1 | 10/2014 | Bauer | |
| 2015/0154528 A1 * | 6/2015 | Kharraz Tavakol | G06Q 10/0631 705/2 |
| 2015/0193583 A1 | 7/2015 | McNair | |
| 2016/0034986 A1 | 2/2016 | Ortiz | |
| 2016/0321430 A1 | 11/2016 | Eckman et al. | |
| 2017/0116373 A1 | 4/2017 | Ginsburg | |
| 2017/0293988 A1 | 10/2017 | Goyal | |

OTHER PUBLICATIONS

U.S. Appl. No. 15/357,745, filed Nov. 21, 2016, Notice of Allowance dated May 24, 2017, all pages.

U.S. Appl. No. 15/479,011, filed Apr. 4, 2017, Non-Final Office Action dated May 31, 2017, all pages.

Non-Final Office Action dated May 28, 2019, in U.S. Appl. No. 16/358,282, 16 pgs.

Non-Final Office Action dated Nov. 21, 2018 in related U.S. Appl. No. 15/902,897, 18 pgs.

Notice of Allowance dated Jan. 24, 2019 in related U.S. Appl. No. 15/902,897, 9 pgs.

Final Office Action dated Aug. 8, 2019 in U.S. Appl. No. 14/967,027, 16 pgs.

* cited by examiner

RISK ASSESSMENT AND EVENT DETECTION

RELATED APPLICATIONS

The present application is related to and claims the benefit of priority of U.S. Provisional Application 62/163,220, filed on May 18, 2015, entitled "Risk Assessment and Event Detection" (the "'220 application") and U.S. Provisional Application No. 62/317,844, filed on Apr. 4, 2016, entitled "Integrated Documentation and Ordering" (the "'844 application"), the entire contents of each of the '220 application and the '844 application is hereby incorporated by reference in its entirety. The present application is also related to U.S. Non-Provisional application Ser. No. 14/967,027, filed on Dec. 11, 2015, entitled "Suggestion Engine" (the "'027 application") which claims priority to U.S. Provisional Application No. 62/095,598, filed on Dec. 22, 2014, entitled "Medical Suggestion Engine" (the "'598 application") and the '220 application, the entire contents of each of the '027 Application and the '598 application is hereby incorporated by reference in its entirety.

BACKGROUND

This specification relates in general to risk assessment and event detection systems and, but not by way of limitation, to evaluating risk assessment suggestions for authorized users and providing such suggestions to authorized users.

The amount of data generated each day continues to grow. In some industries, some of this data may be stored, while a majority of it may be processed and abandoned or ignored. Users working in these industries are beginning to rely more and on this data to make decisions. This may be especially true when the data is introduced as part of an operational flow. However, the time required to sort through stored data can create inefficiencies and the fact that other data may typically be ignored or abandoned may create liabilities.

BRIEF DESCRIPTION OF THE DRAWINGS

Various embodiments in accordance with the present disclosure will be described with reference to the drawings, in which.

DETAILED DESCRIPTION

Figure 1:
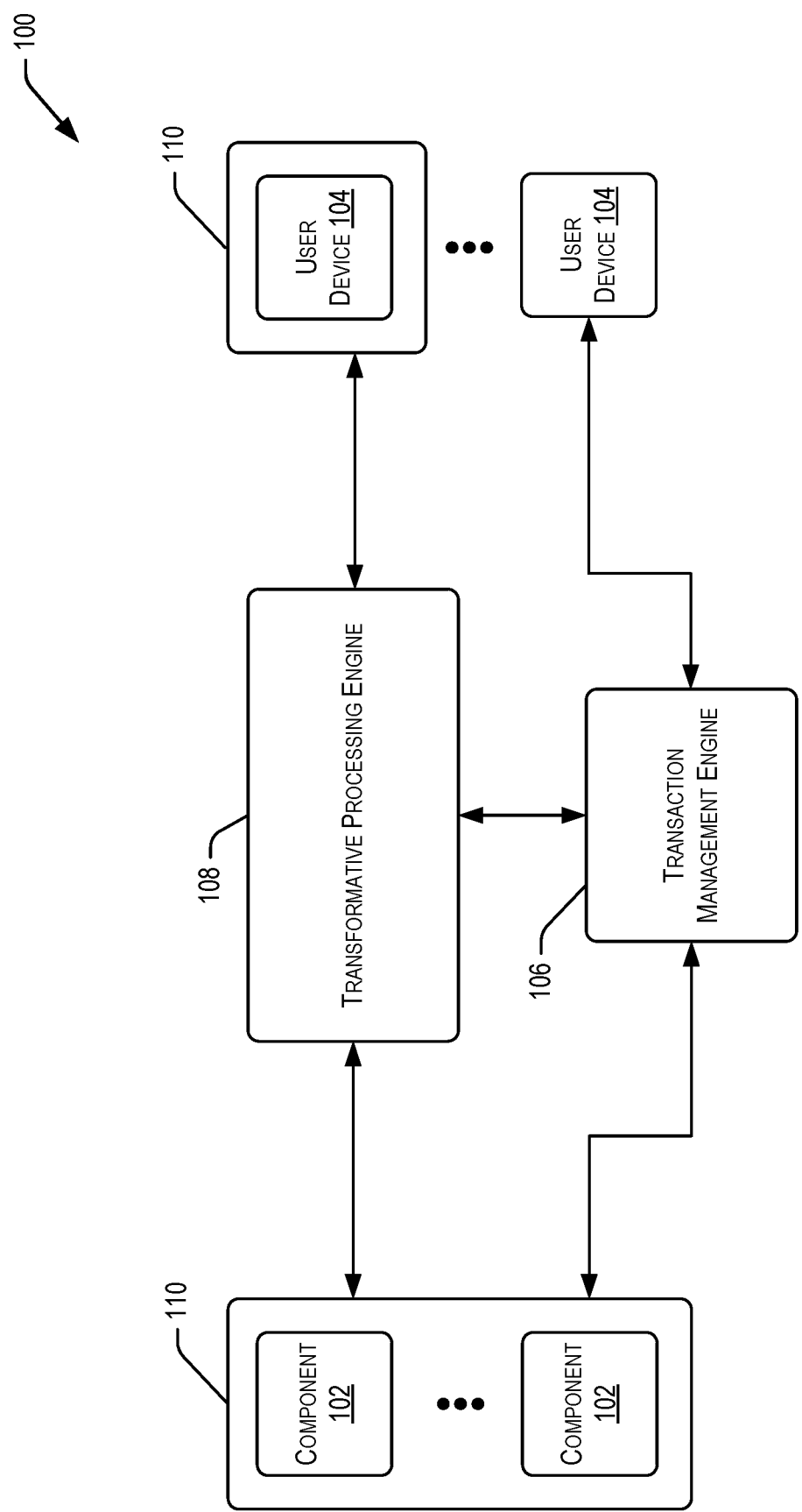
FIG. 1 is an example block diagram illustrating an environment in which techniques relating to generating contextual suggestions and providing contextual suggestions to authorized users as described herein may be implemented, according to at least one example.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In one example, a risk assessment engine is provided. The risk assessment engine is configured to monitor, collect, and/or receive structured and unstructured data from a data warehouse and/or streamed from data storage and processing systems (e.g., electronic record services), or components (e.g., devices that generate data) of a provider network in real-time. The structured and unstructured data corresponds to the treatment of users. The risk assessment engine analyzes the structured data and the unstructured data in order to determine whether a user is at risk for a disorder or a deterioration in their current condition, and whether to include the results of the analysis in a risk assessment. The risk assessment indicates the disorder, identifies the user, and includes certain information to enable an authorized user to make a decision of how to respond to the risk assessment (e.g., decision support output). For example, the risk assessment may indicate a likelihood that the user will develop congestive heart failure, sepsis, or any other disorder in order to allow the appropriate care team member to take guided action prior to the onset of the condition or deterioration. The risk assessment engine is configured to parse through the structured and unstructured data in a manner that enables the risk assessment engine to develop conclusions and/or make assessments about the condition quicker and across broader data sets than a typical authorized user and on a real-time basis as new data point arrive impacting a user's risk assessment. In some examples, because the risk assessment engine parses unstructured data (not just structured data), which may include subjective information, the risk assessment engine may be able to draw conclusions and "see the big picture" of the condition of the user. Once the risk assessment for the user has been generated, it is included in a notification that can be sent to any number of suitable recipients. For example, the notification can be sent to a floor coordinator of a physical location or an authorized user who can take the next steps based on the risk assessment.

In one example, an event escalation engine is provided. The event escalation engine is configured to monitor, collect, and/or receive structured and unstructured data from a clinical data warehouse and/or components of a medical provider network and/or streamed from data storage and processing systems (e.g., electronic record services), or components (e.g., devices that generate data) of a provider network in real-time. In some examples, this includes accessing a live stream of data and retrieving portions of the data that are relevant to a notification event that the event escalation engine is analyzing. The event escalation engine analyzes the data in order to identify when the notification event takes places. Once the event takes place, the event escalation engine accesses a directory of recipients and/or an escalation tree to determine whom to send a notification, what should be included in the notification, whether the notification requires a response, and any other suitable determinations. For example, like the risk assessment engine, the event escalation engine may determine the notification based on the appropriate team member to whom the notification will be sent. The notification may include medical decision support output to enable the team member to take guided action for responding to the circumstances that triggered the notification event. To identify the occurrence of the event, the event escalation engine includes one or more triggering rules that, when fulfilled by identifying certain data, indicate that the event has occurred. The event escalation engine is configured to work well with existing escalation protocols (e.g., use of on-call users, office personnel, etc.). The notification can be provided to one or more recipients in accordance with the recipients' customary methods for receiving notifications. The event detection engine is configured to parse through structured and unstructured data in a manner that enables the event detection engine to detect events and generate notifications regarding the detected events across broader data sets than conventional methods (e.g., a typical authorized user) and on a real-time basis. That automated delivery of generated notifications will likely be more efficient than conventional methods because the possibility of human error is reduced.

In one example, an event identification engine is provided. The event identification engine is configured to monitor, collect, and/or receive structured and unstructured data from a clinical data warehouse and/or components of a provider network and/or streamed from data processing and storage systems (e.g., electronic record services), or components (e.g., devices that generate data) of a provider network in real-time. A directory of registered users is also provided. The directory of registered users indicates users who are participants in one or more past, ongoing, or future clinical trials. In some examples, the directory of registered users is shared among administrators of trials and entities that treat users. In this manner, the entities that treat users can know which user are participants in trials. In some examples, the event identification engine is configured to detect a notification event corresponding to a registered user. For example, if the registered user decides to check into a particular physical location, the act of checking in is a notification event, the occurrence of which may be identified by the event identification engine. Once identified, the event identification engine may also determine other information about why the registered user is checking into the physical location. The event identification engine may also be configured to access a directory of administrators. In some examples, this is considered a recipient data structure. In any event, the directory of administrators is a listing of administrators of trials. In this manner, the event identification engine can identify the recipient and can generate a notification that indicates certain information about the registered user. For example, the notification may indicate that the registered user checked into the physical location and was treated for a particular condition.

In one example, a transformative processing engine is provided. The transformative processing engine is configured to collect different types of information. In some examples, portions of the information can be provided to requesting users automatically in the form of one or more reports. The reports can be generated in a manner that ensures that personal information is not included or otherwise revealed.

Referring first to FIG. 1, a block diagram of an embodiment of an interaction system 100 is illustrated. Generally, in interaction system 100, data can be generated at one or more system components 102 and/or user devices 104. Transaction management engine 106 can manage the flow of communications within interaction system. Transformative processing engine 108 can receive, intercept, track, integrate, process and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102 and/or data in a corresponding communication received from a user device.

As another example, a user device 104 can be configured to detect user input received at a user interface of the device. The user input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect user input requesting particular data, to generate a request communication (e.g., to be sent to transformative processing engine), to receive the requested data and/or to present the received data.

Data can include information that identifies a person, such as personal information and/or demographic information. For example, the information can identify a person's name, age, sex, race, physical address, phone number, email address and/or social security number. Data may include information collected by a government agent, employer, insurer, or school or university, that relates to a past, present, or future condition or status (e.g., pertaining to employment, political involvement, occupation, health, or financial status) of any individual. For example, data may include information about past events.

Data may identify an entity being evaluated and/or one at least partly performing an evaluation. For example, a communication may identify a first company as one being evaluated and a second company as one evaluating a quality of a product of the first company. As another example, a communication may identify a first service plan of a first company as one providing an Internet network and may identify one or more users providing speed checks over the network.

The depicted engines, devices and/or components can communicate over one or more networks. A network of one or more networks can include a wired network (e.g., fiber, ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or transaction management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or processing focus. Exemplary types of facilities include server farm facilities, web-server facilities, data-storage facilities, technical-support facilities, telecommunication facilities, care facilities and/or business operation facilities. For example, a first facility may include a structure at a first location at which one or more resources (e.g., computational resources, equipment resources, laboratory resources and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another examples, different facilities may include resources of similar or same types but may vary in terms of, for example, user accessibility, location, managing client, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client or receiving a service from the client.

In some examples, one or more components 102 and one or more user devices 104 may communicate with transformative processing engine 108 and transaction management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., transaction management engine 106, an entity device and/or a user device) and/or locally or remotely stored. In some examples, transformative processing engine 108 receives data in a particular format (e.g., the HL7 format) or conforming to any other suitable format and/or is configured to transform received data to conform with the particular format.

One or more components 102 of facility 110 can include and/or has access to a local or remote memory for storing generated data. In some examples, the data is stored by one or more servers local to facility 110. Such storage may enable facility 110 to retain locally data pertaining to its facility prior to (or in conjunction with) the data being shared with transformative processing engine 108 and/or transaction management engine 106. In some examples, the one or more servers of facility 110 share data directly with a record service (not shown), and the record service makes the data available to transformative processing engine 108 and/or transaction management engine 106. Once an electronic record is updated at facility 110, an indication of the update may be provide to the record service. The record service may then update a corresponding record associated with the electronic record.

The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from an component (or facility), the record service can identify a corresponding record and update the record to include the data (or processed version thereof). In some examples, the record service provides data to transformative processing engine 108.

Facility 110 can include one at which a resource is located and/or service is provided. Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private and/or proprietary network or protocols. The use of one or more private and/or proprietary protocols can promote secure transfer of data.

Figure 2:
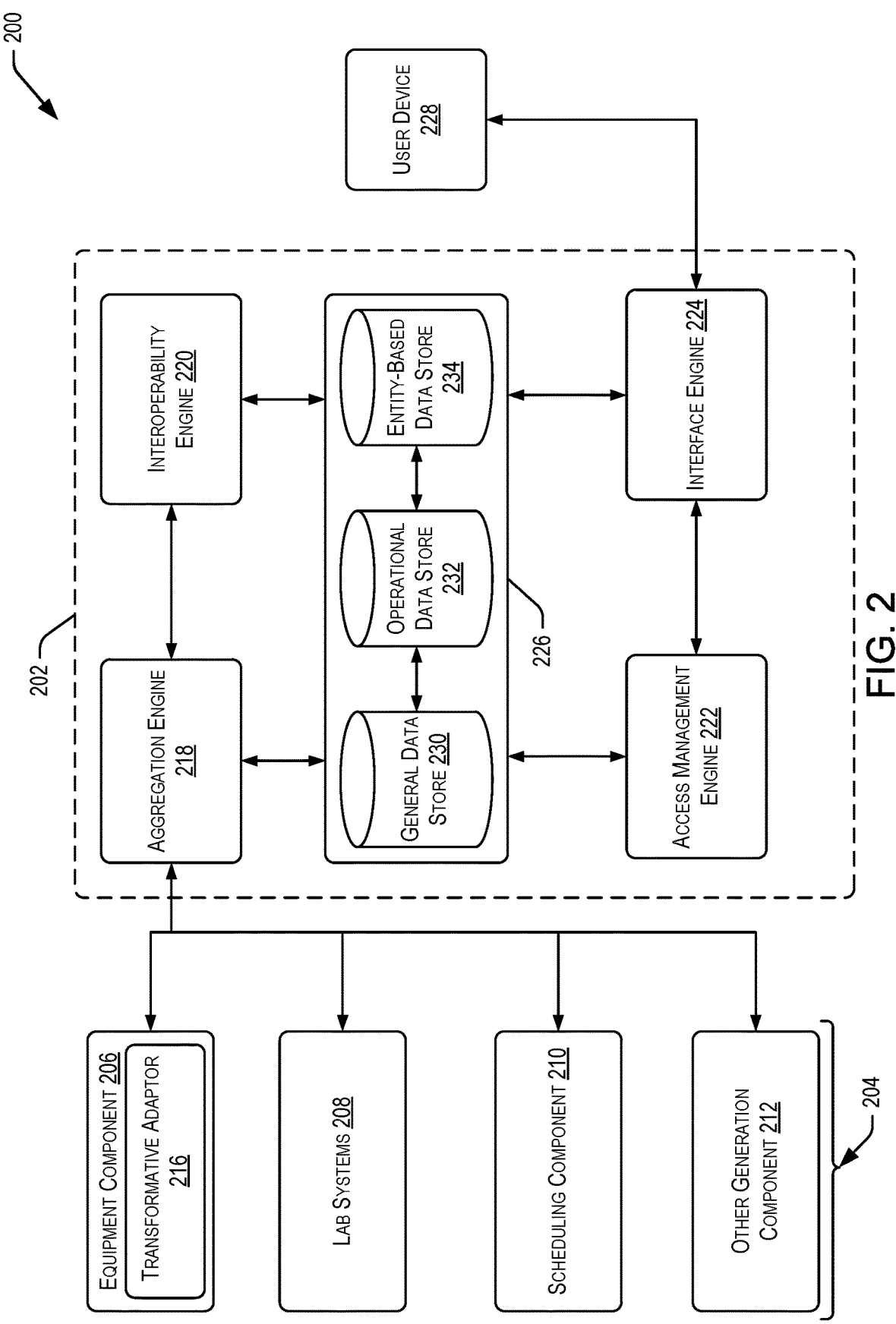
FIG. 2 is an example block diagram illustrating an environment in which techniques relating to generating contextual suggestions and providing contextual suggestions to authorized users as described herein may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 includes an equipment component 206, a lab systems component 208, a scheduling component 210 and other generation component 212. One or more generation components 204 are examples of one or more components 102 discussed with reference to FIG. 1.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design—making large amounts of data, in many different originating formats available to various types of users, via one or more interfaces.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Scheduling component 210 includes any suitable computing devices used for business-related purposes with respect to interaction system 200. For example, scheduling component 210 can be configured to schedule a resource for allocation for a particular entity during a particular time slot. Scheduling component 210 can monitor a schedule for the resource and can identify one or more available time slots that may be secured by a particular entity. Upon receiving a scheduling indication, scheduling component 210 may update a schedule of a resource to reflect that a particular time slot is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the data provided by the component or the user device located at the geographic location.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of a same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, have paid a subscription fee associated with access to data store 226, and the like. Access management engine 222 may also verify that the user device 228 has an IP address or geographical location that corresponds to an authorized list, that the user device 228 includes a plug-in for properly accessing data store 226, that the user device 228 is running certain applications required to access data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

Figure 3:
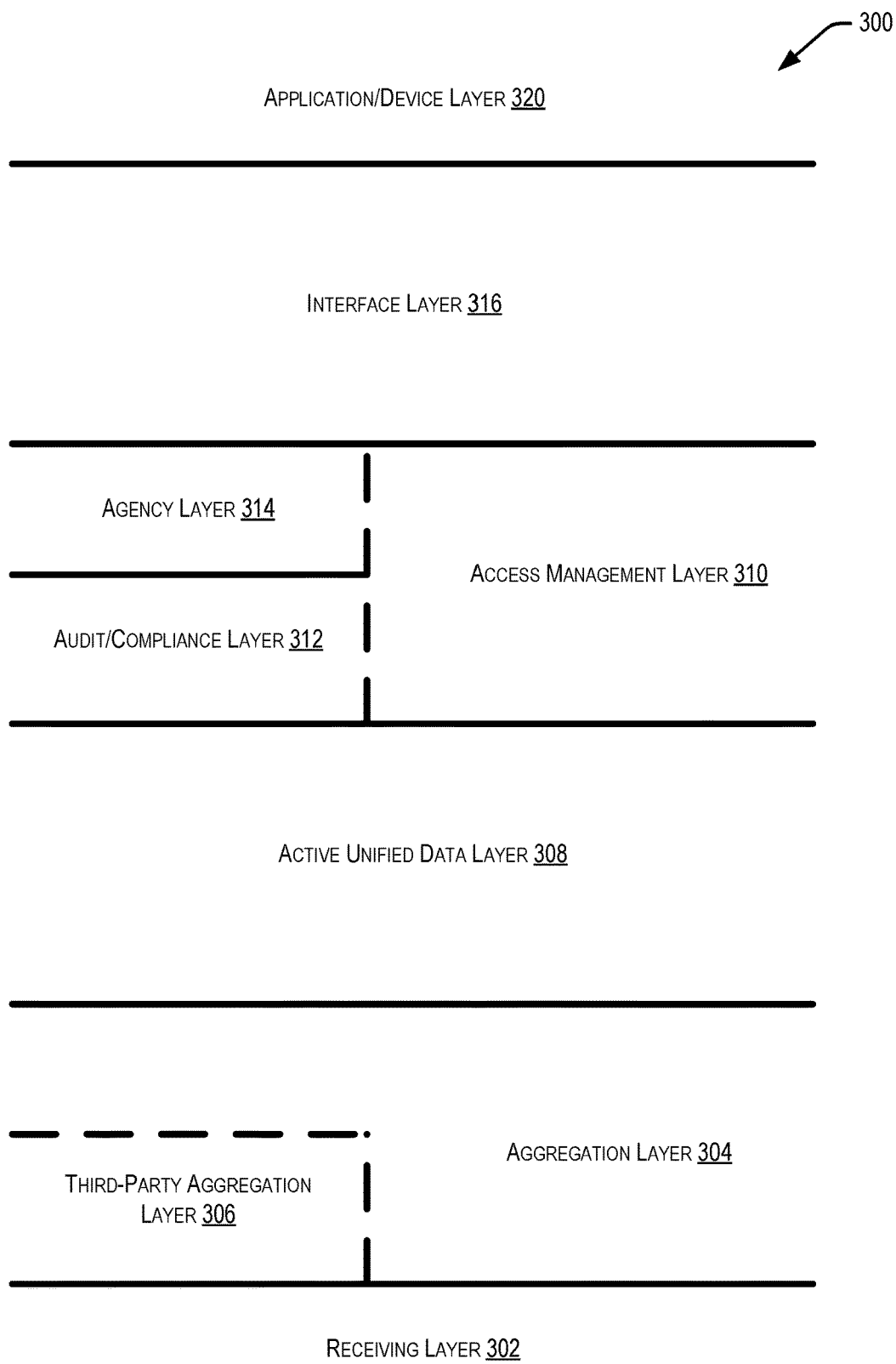
FIG. 3 is an example schematic model illustrating an a network communication model in which techniques relating to generating contextual suggestions and providing contextual suggestions to authorized users as described herein may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties Finally, architecture stack 300 includes application/device layer 320. application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
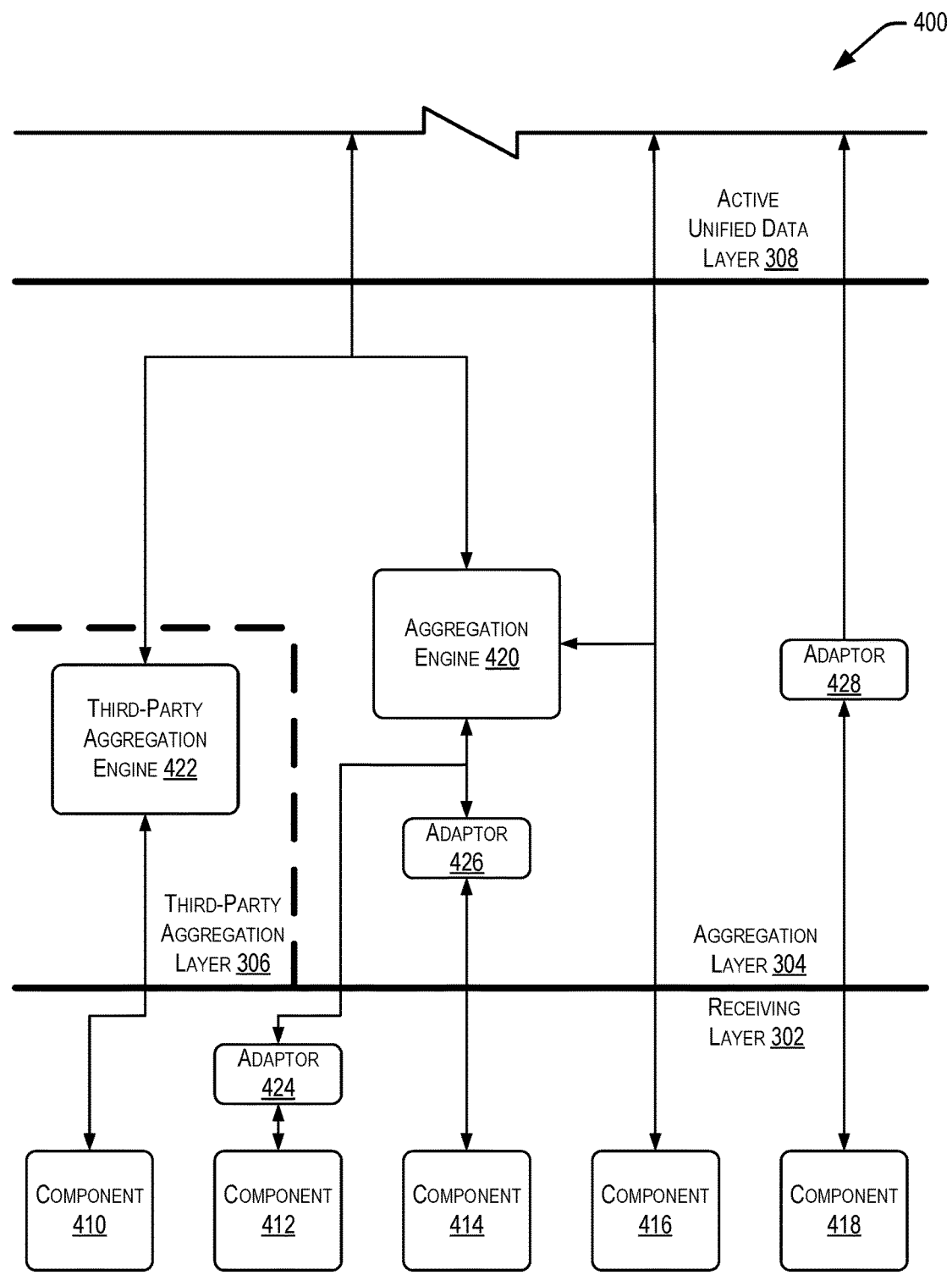
FIG. 4 is an example schematic model illustrating an aspect of the network communication model of FIG. 3 in more detail.

Turning next to FIG. 4, a diagram 400 is shown that depicts a portion of architecture stack 300 according to an embodiment of the invention. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

Figure 5:
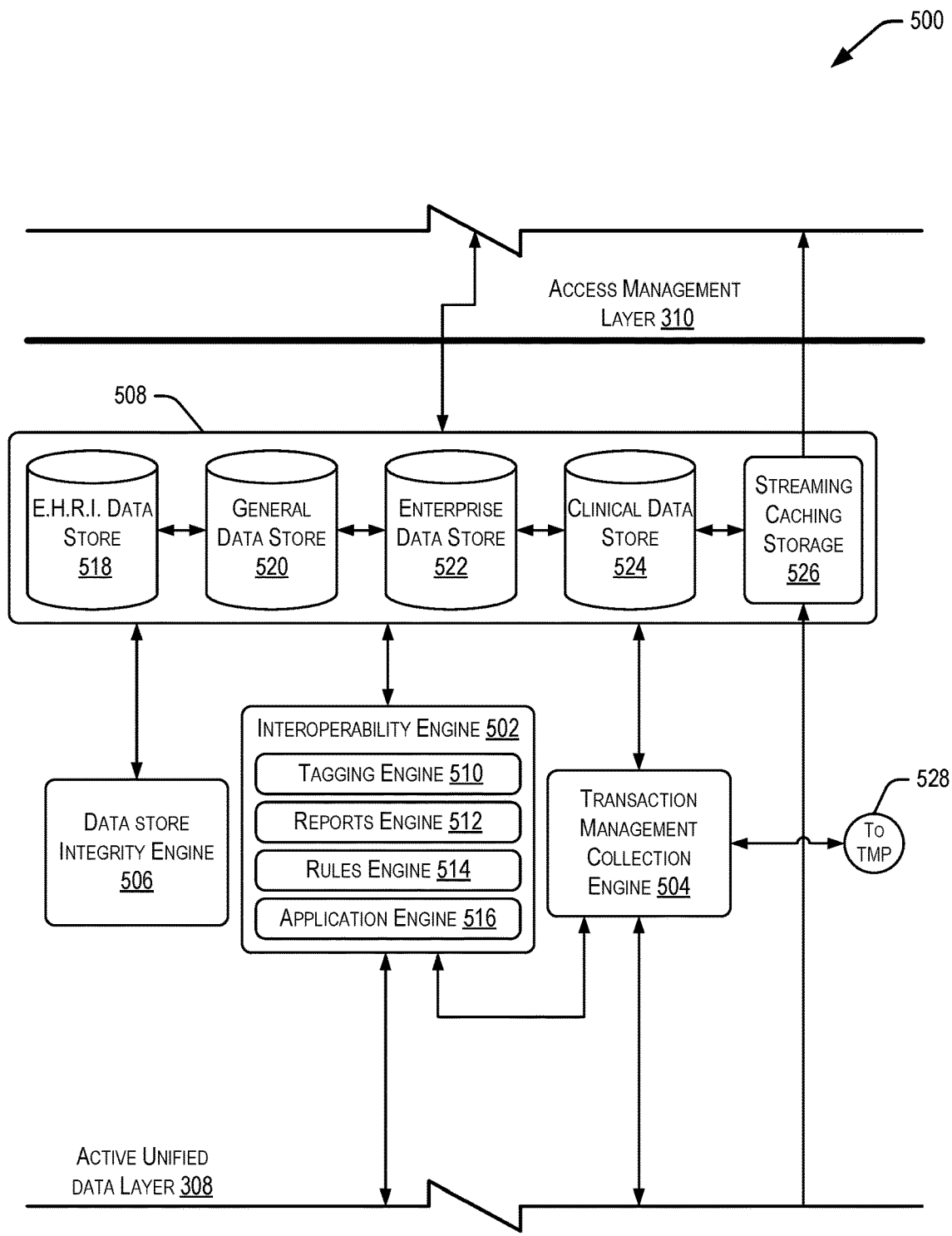
FIG. 5 is an example schematic model illustrating an aspect of the network communication model of FIG. 3 in more detail.

Referring next to FIG. 5, a diagram 500 is shown that depicts a portion of architecture stack 300 according to an embodiment of the invention. In particular, diagram 500 includes active unified data layer 308 and a portion of access management layer 310. Active unified data layer 308, as illustrated in diagram 500, includes an interoperability engine 502 (e.g., interoperability engine 220), a transaction management collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Transaction management collection engine 504 is implemented as part of transaction management engine 106. Transaction management collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304. The table may be stored in association with the transaction management platform 528.

In some examples, the table also includes information for tracking the progress of the message from an origination node to a destination node. For example, typically when a message (e.g., any communication of data) is first received by transformative processing engine 108 (e.g., interoperability engine 502), transaction management engine 106 (e.g., transaction management collection engine 504 of transaction management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to transaction management engine 106 that it saw the message. In this manner, transaction management engine 106 may enable end-to-end tracking of messages for the life of the message.

In one example, the messages are requests. The requests may be generated based on user input at one of the components. The requests may be received by transformative processing engine 108 and integrated into the system. In some examples, transaction management engine 106 may be notified that the requests have been received and may therefore be configured to generate message IDs for each request. These message IDs may then be associated with each of the requests. As the requests continue to move throughout the interaction system (e.g., away from transformative processing engine 108), transaction management engine 106 may be track their movement using the message IDs. If one of the requests does not make it to its destination, transaction management engine 106 (or part of the transaction management platform 528) may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, transaction management engine 106 (e.g., transaction management collection engine 504 of transaction management engine 106) may receive the message and/or message identifier directly from one of components 410-418. For example, one of components 410-416 may be configured to generate the unique message identifier and/or communicate directly with transaction management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, transaction management collection engine 504 provides unique message identifiers to other elements of the interaction system to monitor the messages as they move throughout the interaction system. Transaction management collection engine 504 also provides a portion of the unique message identifiers to a transaction management platform (indicated by a circle 528) for further analysis of the message identifiers. Such analysis may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage business rules, condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("record data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

[Within record data store 518 is retained data including electronic record information. In some examples, the information within record data store 518 is organized according to entity identifying information. Thus, record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. F2. In some examples, the operational data ware house 522 includes data pertaining to decision making as discussed herein and other data typically used by conventional business concerns.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of personal record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
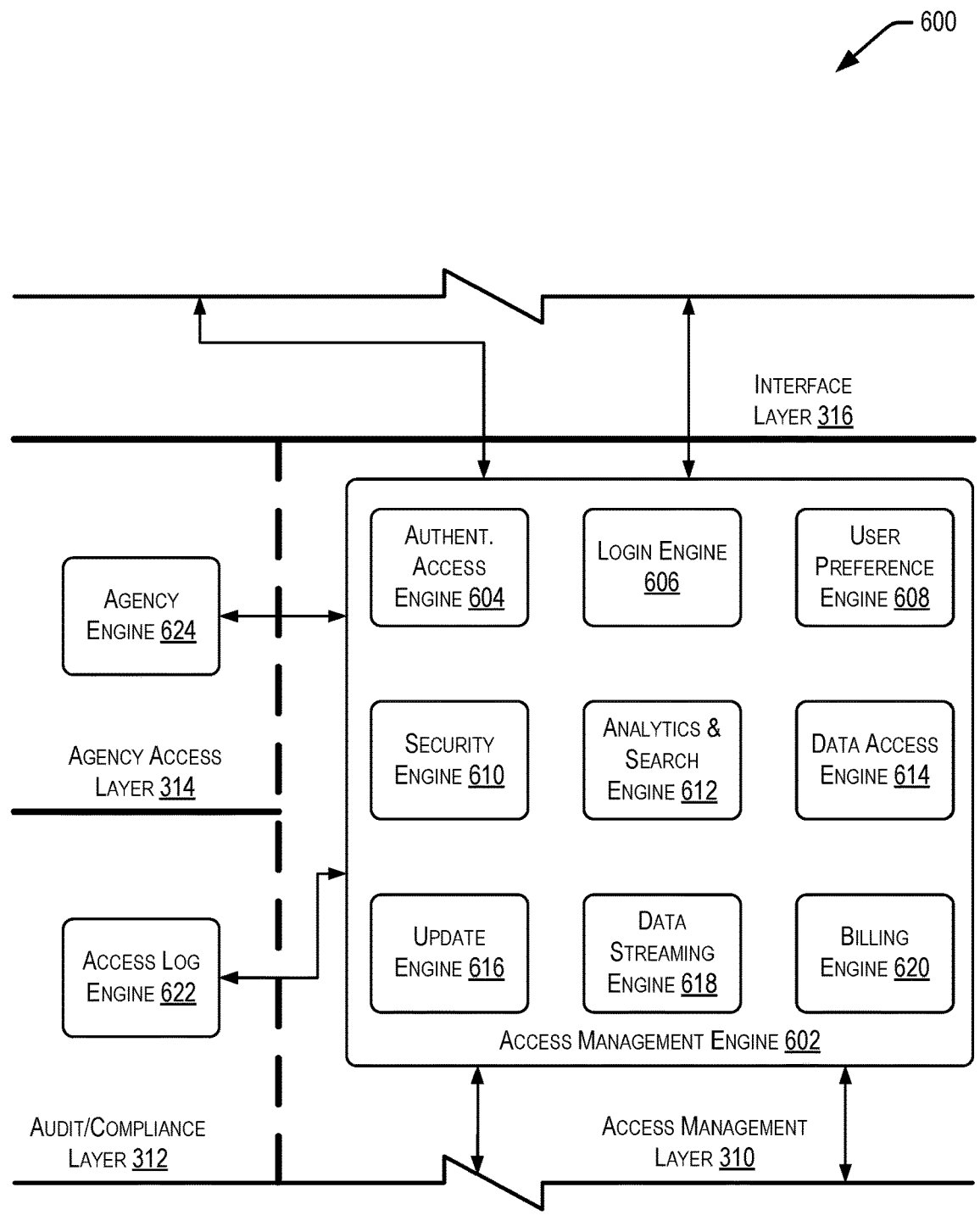
FIG. 6 is an example schematic model illustrating an aspect of the network communication model of FIG. 3 in more detail.

FIG. 6 shows a diagram 600 which depicts a portion of architecture stack 300 according to an embodiment of the invention. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. For example, agencies that may use agency engine 624 include agencies to which the interaction system provides compliance, tracking, or other reporting information. For example, agency engine 624 may be used to track one or more performance indicators identified by a government agency and/or to provide report instances of defined types of events. Thus, in some examples, a government agency uses agency engine 624 to collect data pertaining to compliance of the interaction system with one or more statutes or regulations. In some examples, a university is an agency that uses agency engine 624 to collect data pertaining to one or more studies. In some examples, agency engine 624 can identify one or more entities (e.g., governmental agencies) that are to receive reports pertaining to operations or events and what types of data are to be reported to those entities. Agency engine 624 can then collect the pertinent data, potentially format and/or analyze the data, and facilitate transmission of (e.g., raw, formatted and/or analysis of) the data to the appropriate agency.

Figure 7:
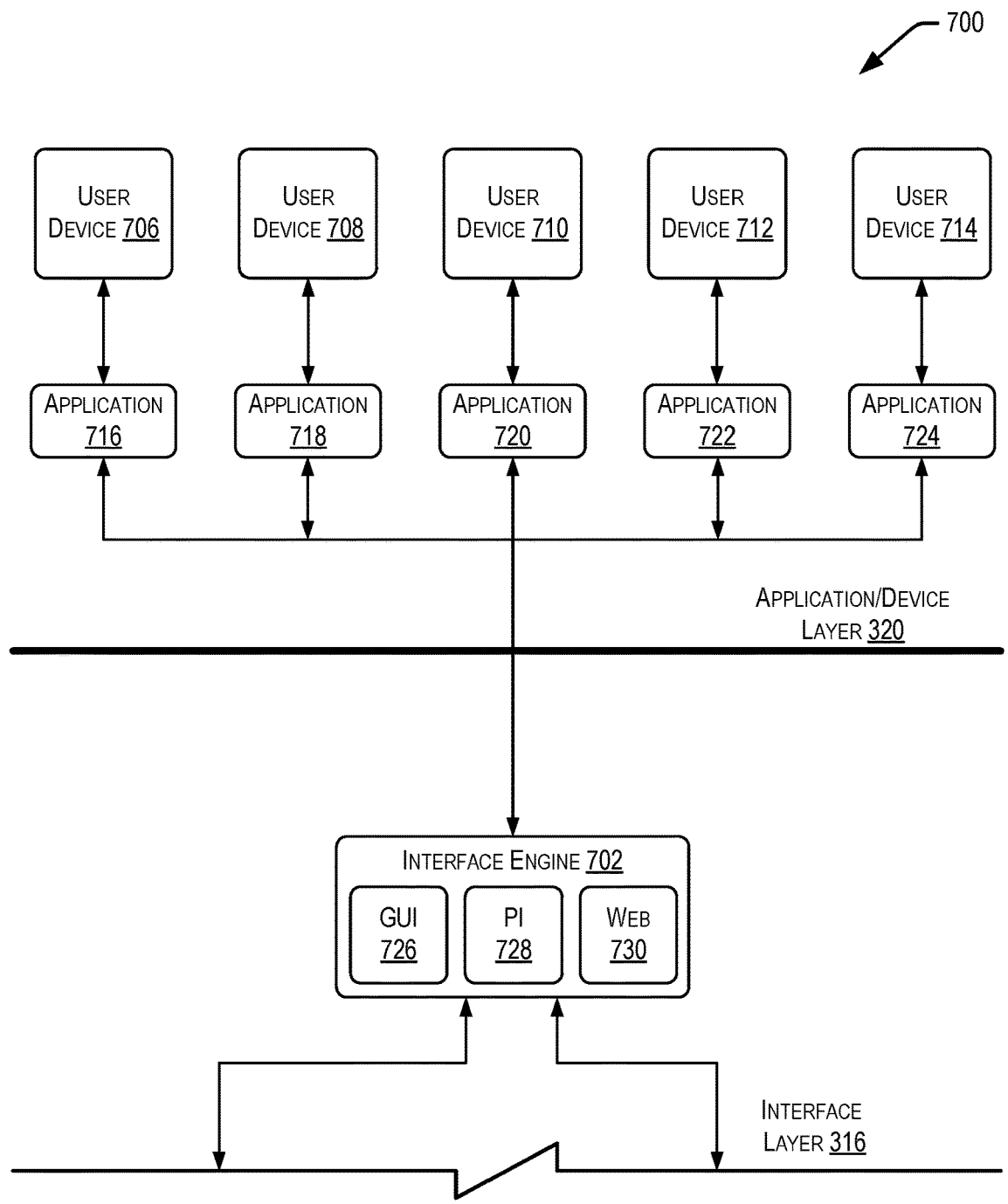
FIG. 7 is an example schematic model illustrating an aspect of the network communication model of FIG. 3 in more detail.

FIG. 7 shows a diagram 700 which depicts a portion of architecture stack 300 according to an embodiment of the invention. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 716-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for an particular entity. In some examples, application 720 may present different data depending on a specialty associated with the entity and protected information associated with the entity. In this manner, application 720 adapts and automatically adjusts depending on the context in which the entity is using the application. In some examples, the data indicates performance statistics for the entity, metrics relating to where the entity falls along a distribution of other similar entities, outlier instances, trends in events or actions, and the like. Application 720 may be configured to receive input, adjust presentations, present unprompted alerts, adjust display of content, move more relevant content to the foreground, move less relevant content to the background, populate forms for the entity.

In another example, application 722 may be specific for nurses or types of nurses. In this example, application 722 may include dashboards, widgets, windows, icons, and the like that are customized to individual nurses. Similar to the example discussed above pertaining to the doctor, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

In some examples, application 724 may be a business intelligence application. In this example, application 724 is used to display business information generated by components of the interaction system. This business information can be used for operations, planning, and forecasting. Such business information may include data because such data may impact operations, planning, forecasting, and the like. Accordingly, application 724 may present de-identified information in the form of one or more metrics, indicators, or the like as they pertain to business intelligence.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data.

In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
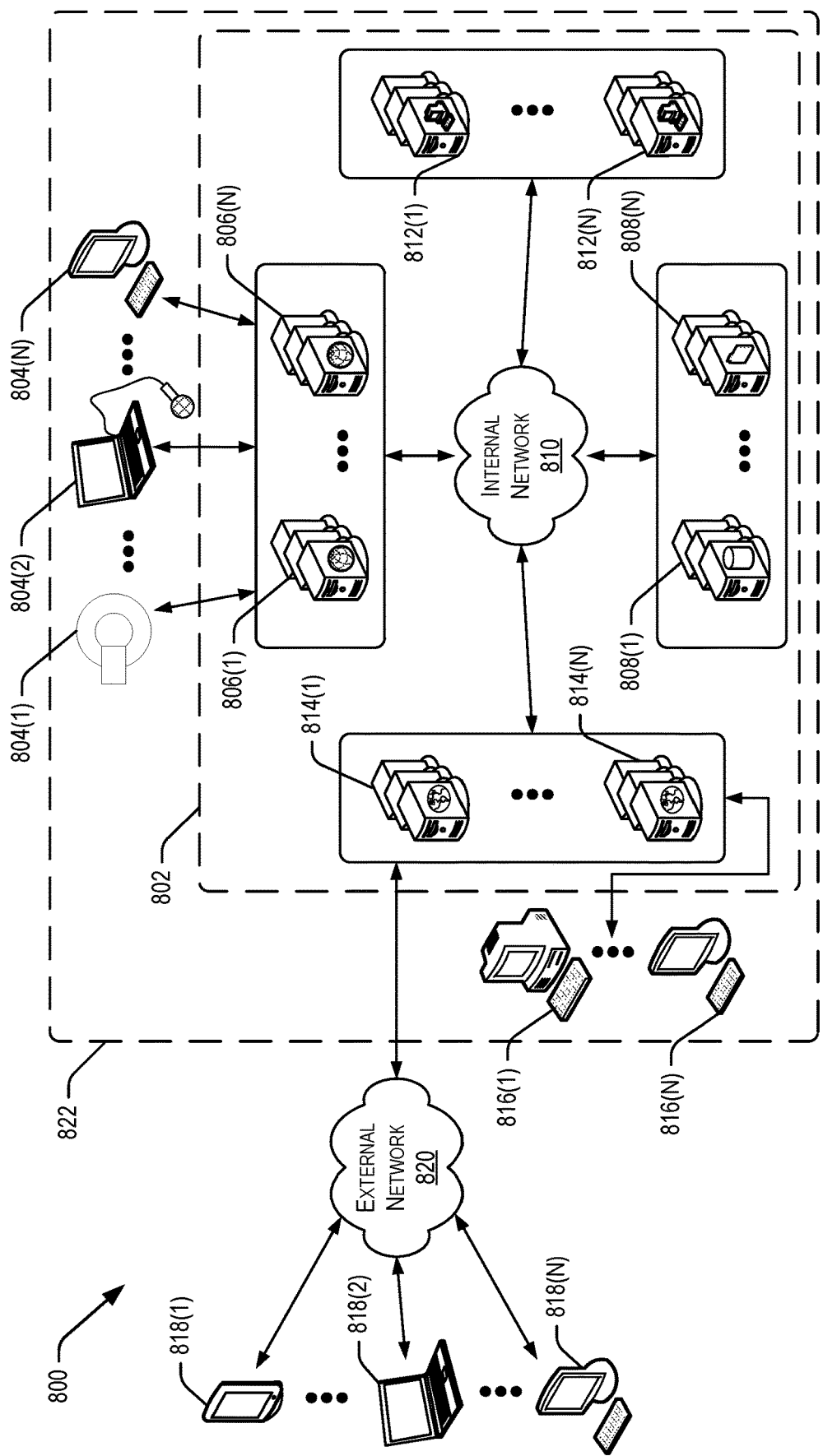
FIG. 8 is an example schematic architecture illustrating a network in which techniques relating to generating contextual suggestions and providing contextual suggestions to authorized users as described herein may be implemented, according to at least one example.

Turning now to FIG. 8, an interaction system 800 is shown in accordance with an embodiment of the invention. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

Figure 9:
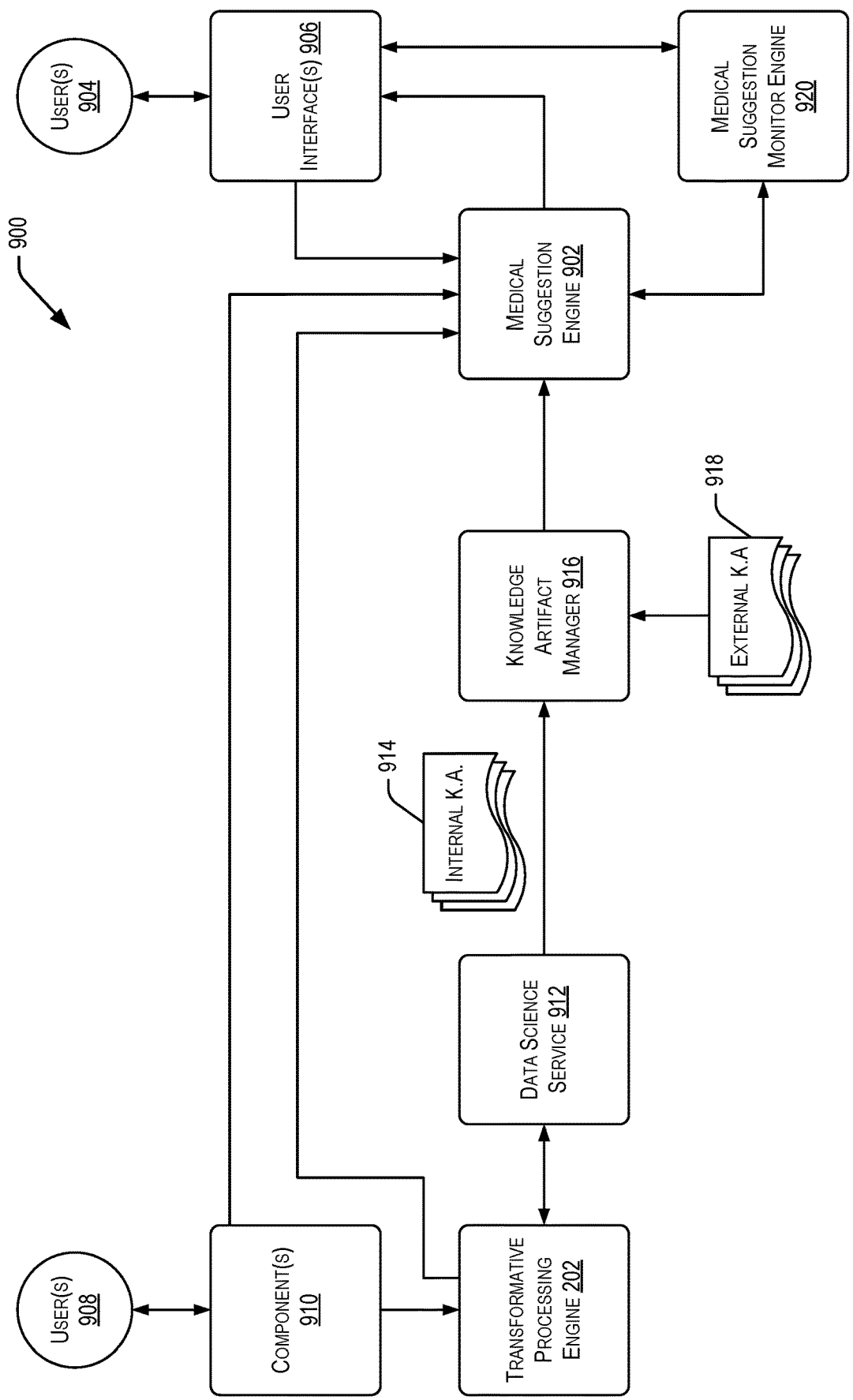
FIG. 9 is an example block diagram illustrating techniques relating to generating contextual suggestions and providing contextual suggestions to authorized users as described herein, according to at least one example.

Turning now to FIG. 9, a medical provider network 900 is shown in accordance with an embodiment of the invention. The medical provider network 900 may be implemented using at least some of the elements of the medical provider network 800. The medical provider network 900 includes a medical suggestion engine 902, which is configured to implement the techniques described herein. For example, the medical suggestion engine 902 generates medical decision support output (e.g., medical suggestions, recommendations, considerations, workflows parameters, and the like) that can be provided to receiving users 904 via one of more user interfaces 906. In order to generate the medical decision support output, the medical suggestion engine 902 receives certain medical-related information. The creation of such medical-related information begins with generation users 908. The generation users 908 and the receiving users 904 may come from the same group of users and may be similar to the users that operate the components 410-418 and/or the users that operate the user devices 706-714. Accordingly, the generation users 908 interact with components 910 to generate medical-related data. The components 910 are examples of the components 410-418 discussed herein.

The medical-related data generated by the users 908 interacting with the components 910 is provided to the transformative processing engine 202 and the transformative processing engine 202 performs one or more operations on the medical-related data such as those discussed herein. One of the operations includes the transformative processing engine 202 retaining the medical-related data in a manner that makes it searchable and useable by other elements of the medical provider network 900. For example, a data science service 912 interacts with the transformative processing engine 202 to access the medical-related data stored thereby. The data science service 912 analyzes the medical-related data retained by the transformative processing engine 202 to give the data meaning. For example, the data science service 912 evaluates the medical-related data to identify trends in the data or correlations between different data that could be valuable for treatment of patients of the medical provider network 900. Identified trends, correlations, and other outputs (e.g., evidence of treatment patterns, outcomes, and the like) identified from the medical-related data by the data science service 912 are referred to herein as internal knowledge artifacts 914 and are provided to a knowledge artifact manager 916. Other examples of the internal knowledge artifacts 914 include case studies of patients treated by medical care professionals associated with the medical provider network 900, results of internal medical journals, and other types of information that characterizes past medical treatment and that can be used to assist in future treatment of the same and/or similar patients.

The data science service 912 includes human users accessing computing devices to generate the internal knowledge artifacts 914. Generating the internal knowledge artifacts 914 may include adjusting relevant medical-related data into one or more formats, particular data structures, or the like that can be read by the medical suggestion engine 902 when generating medical decision support output. A computing device of the data science service 912 may be any conventional computing device including a memory, processor, operating system, and the like for generating the internal knowledge artifacts 914. The data science service 912 may also include one or more automated engines within a computing device, or distributed throughout many computing devices. The engines may be configured to analyze the medical-related data and generate internal knowledge artifacts 914 programmatically. For example, the data science service 912 may include a learning engine that analyzes the medical-related data to identify trends, correlations, patterns, and the like in a similar manner as the human users described above. The internal knowledge artifacts 914, whether generated with the assistance of human users or generated programmatically, are provided to the knowledge artifact manager 916 that manages the internal knowledge artifacts 914. This may include organizing the internal knowledge artifacts 914 in a manner useable by the medical suggestion engine 902. To this end, the knowledge artifact manager 916 may include a memory, which may be distributed among many different devices.

The knowledge artifact manager 916 also receives external knowledge artifacts 918. The external knowledge artifacts 918 are generated by organizations, users, and others that fall outside of a medical provider organization associated with the medical provider network 900. Thus, the external knowledge artifacts 918 may include medical journals, proprietary and non-proprietary medical-related data organized in some structure, research findings, medical theses, treatment patterns for patients with particular diagnosis, prescription drug characteristics, and any other suitable type of information that can be arranged and managed by the knowledge artifact manager 916. Thus, the external knowledge artifacts 918 and the internal knowledge artifacts 914 represent associations between certain medical situations (e.g., orders, diagnoses, etc.) and the medical outcomes in the related cases. In some examples, the knowledge artifact manager 916 is not included in the medical provider network 900 and the internal knowledge artifacts 914 and the external knowledge artifacts 918 are made available directly to the medical suggestion engine 902.

When the knowledge artifact manager 916 is included in the medical provider network 900, the knowledge artifact manager 916 manages all of the knowledge artifacts. To this end, the knowledge artifact manager 916 performs operations on the knowledge artifacts 914, 918 to retain them in the memory of the knowledge artifact manager 916 in a manner and format that is accessible by the medical suggestion engine 902. In some examples, once the knowledge artifact manager 916 receives the internal knowledge artifacts 914 and the external knowledge artifacts 918, the knowledge artifact manager 916 compares the different knowledge artifacts and may identify knowledge artifacts based on a combination of the internal knowledge artifacts 914 and the external knowledge artifacts 918. The knowledge artifact manager 916 receives the internal knowledge artifacts 914 and the external knowledge artifacts 918 on an ongoing basis. In some examples, the knowledge artifacts 914, 918 are sent to the knowledge artifact manager 916 periodically (e.g., hourly, daily, weekly, etc.), when requested by the knowledge artifact manager 916, in accordance with a user-defined rule or a machine-defined rule (e.g., send in batches consisting of ten knowledge artifacts), or in any other suitable manner. The knowledge artifact manager 916 in turn provides the knowledge artifacts 914, 918 to the medical suggestion engine 902 periodically, when requested by the medical suggestion engine 902, in accordance with a rule, or in any other suitable manner. In some examples, the medical suggestion engine 902 does not receive the knowledge artifacts 914, 918, but accesses them when needed.

In either case, the medical suggestion engine 902 accesses the knowledge artifacts 914, 918 and based on other current medical information, generates medical decision support output. The current medical information may be received by the medical suggestion engine 902 in real-time or substantially real-time. The current information is received from the transformative processing engine 202, the components 910, or via the user interfaces 906. The current information includes real world conditions data (e.g., social media feeds, news services, RSS feeds, information from organizations such as the Center for Disease Control, and the like that pertains to weather conditions, geographic health conditions, spread of diseases, and the like), details about a patient (e.g., medical record information), and details about a care scenario of the patient for which the medical suggestion engine 902 will make one or more suggestions. For example, the medical suggestion engine 902 may receive current information in the form of output from a dialysis machine (one of the components 910). The output may be associated with a particular patient of the medical provider network who was treated using the dialysis machine. The medical suggestion engine 902 accesses the output, which identifies the particular patient, and runs through a list of potentially-relevant knowledge artifacts that may assist the medical suggestion engine 902 in making a medical suggestion to the particular patient's doctor. For example, the medical suggestion engine 902 may determine that, based on a knowledge artifact (external, internal, or a combination) dealing with kidney failure, a prescription drug may be helpful for the particular patient. This information (i.e., recommended drug for the particular patient) is then provided to the doctor, who is one of the receiving users 904, as a medical suggestion. The medical suggestion is a type of medical decision support output that can be generated by the medical suggestion engine 902. The medical decision support output may therefore be based on the current information (e.g., real world conditions data, patient details, and care scenario details), knowledge artifacts, and output parameters and configuration settings (e.g., user-defined and machine-defined (e.g., learned) rules that define what output will be presented, how it will be presented, and other details about presentation).

The medical suggestion engine 902 may interact using the active unified data layer 308 or the access management layer 310. In some examples, at least a portion of the interactions of the medical suggestion engine 902 take place in the interface layer 316 and/or the application/device layer 320. In this manner, the medical suggestion engine 902 may be configured to provide the medical decision support output to the user interfaces 906. The user interfaces 906 are examples of the user interfaces capable of generation by the interface engine 702 and may be accessed by the receiving users 904 using applications running on user devices as described herein. The medical suggestion engine 902 provides the medical decision support output either by subscription or by publishing.

The medical provider network 900 also includes a medical suggestion monitor engine 920. The medical suggestion monitor engine 920 is configured to monitor the medical suggestion engine 902. This may include, for example, comparing medical decision support output (e.g., medical suggestions) generated by the medical suggestion engine 902 with result information characterizing whether medical care professionals acted on the suggestions, ignored the suggestions, or in some other way acknowledged the suggestions. Such result information is collected from the receiving users 904 via the user interfaces 906 or directly from users devices on which the receiving users 904 interact in some other way. In some examples, the result information is collected over time and provided to the medical suggestion monitor engine 920 periodically. In this manner, the medical suggestion monitor engine 920 may ensure that the suggestions generated by the medical suggestion engine 902 are current, correct, and meaningful. The medical suggestion monitor engine 920 is configured to adjust the weight of previously made medical suggestions if those suggestions are not being acknowledged. The medical suggestion monitor engine 920 also outputs reports, alerts, signals, and the like pertaining to medical suggestions. Such reporting may include recommendations to operators of the medical provider network 900 regarding adjustments to the medical suggestion engine 902, the knowledge artifact manager 916, the user interfaces 906, or any other element of the medical provider network 900.

Figure 10:
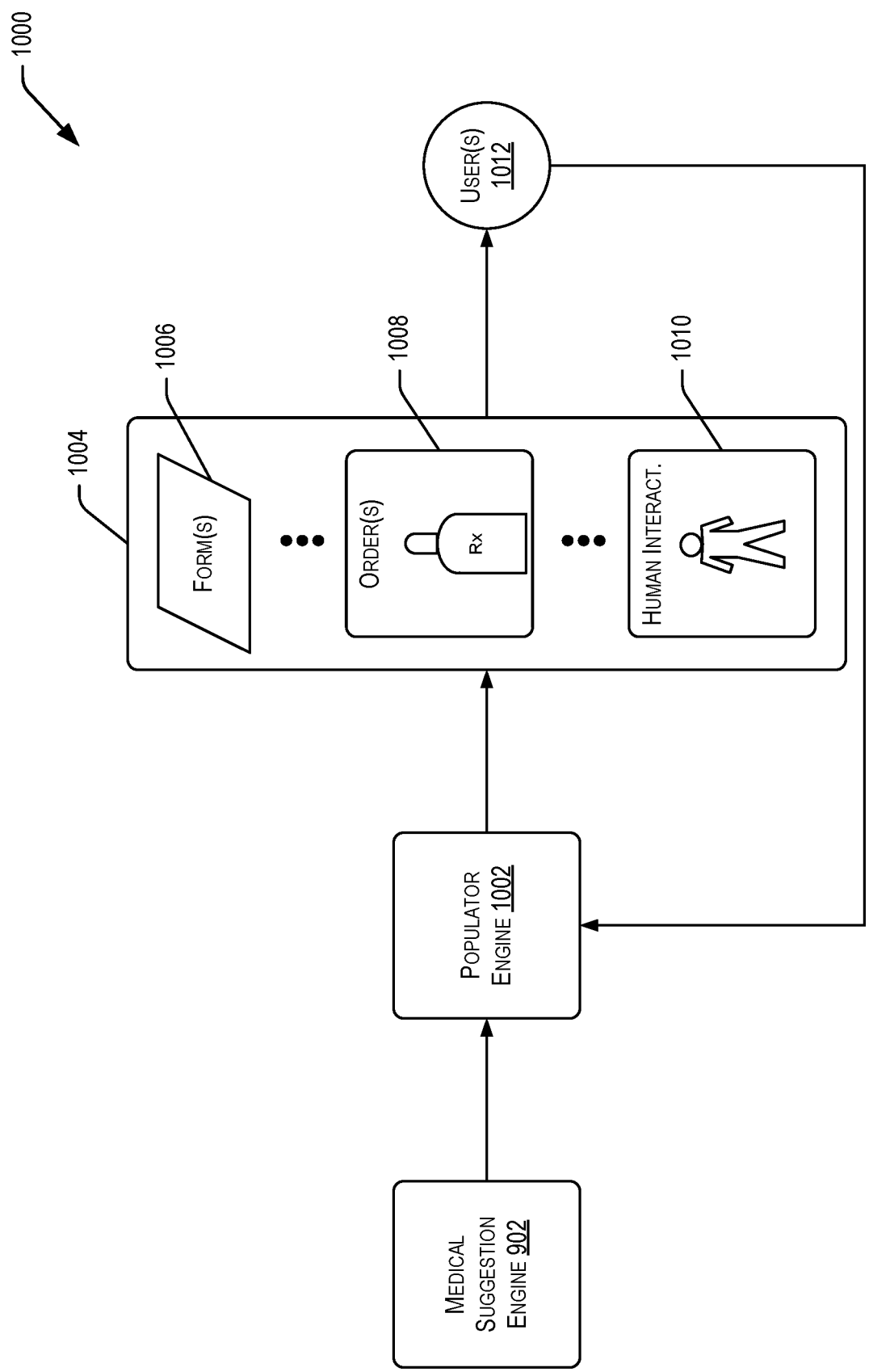
FIG. 10 is an example block diagram illustrating techniques relating to populating forms using contextual suggestions as described herein, according to at least one example.

Turning now to FIG. 10, a medical provider network 1000 is shown in accordance with an embodiment of the invention. The medical provider network 1000 includes the medical suggestion engine 902 and a populator engine 1002. In some examples, the populator engine 1002 is implemented as an engine within the medical suggestion engine 902 as discussed with reference to FIG. 9. In either case, after the medical suggestion engine 902 receives details about a course of treatment for a patient, it provides a list of possible medical tasks (e.g., a form of medical decision support output) to the populator engine 1002. The list of possible medical tasks are future medical tasks that are either recommended, suggested, and/or required for treatment of the patient. At least some of the future medical tasks may have corresponding medical forms, the submission of which are preconditions for fulfillment of the tasks. The populator engine 1002 therefore identifies from the medical tasks, a list of appropriate medical forms 1004. The list of medical forms 1004 may include any medical form that may be required prior to fulfillment of a medical task. For example, the list of medical forms 1004 may include medical forms 1006, medical orders 1008, and medical human interaction 1010. The medical forms 1006 are examples of forms for imaging, testing, lab work, and the like. The medical orders 1008 are examples of forms for prescriptions, treatment on particular medical devices, and the like. The medical human interaction 1010 are examples of forms for referrals to other medical care professionals, referrals to other medical care facilities, requests for consultations by specialists, discharge papers, check-in patient forms, and the like.

A list of medical forms 1004 is provided to users 1012. The users 1012 are examples of the generation users 908 and/or the receiving users 904. In some examples, the users 1012 receive the list and select which forms the populator engine 1002 should populate. In some examples, the populator engine 1002 populates all relevant forms from the list of medical forms 1004 and provides the list of pre-populated forms to the users 1012. Populating a form includes populating fields of the form using current information identified by the medical suggestion engine 902. The current information includes patient care scenario details and patient details, which may include identifying and non-identifiable personal health information. The populator engine 1002 is configured to protect personal health information and not present it to users that are not authorized to access it.

Figure 11:
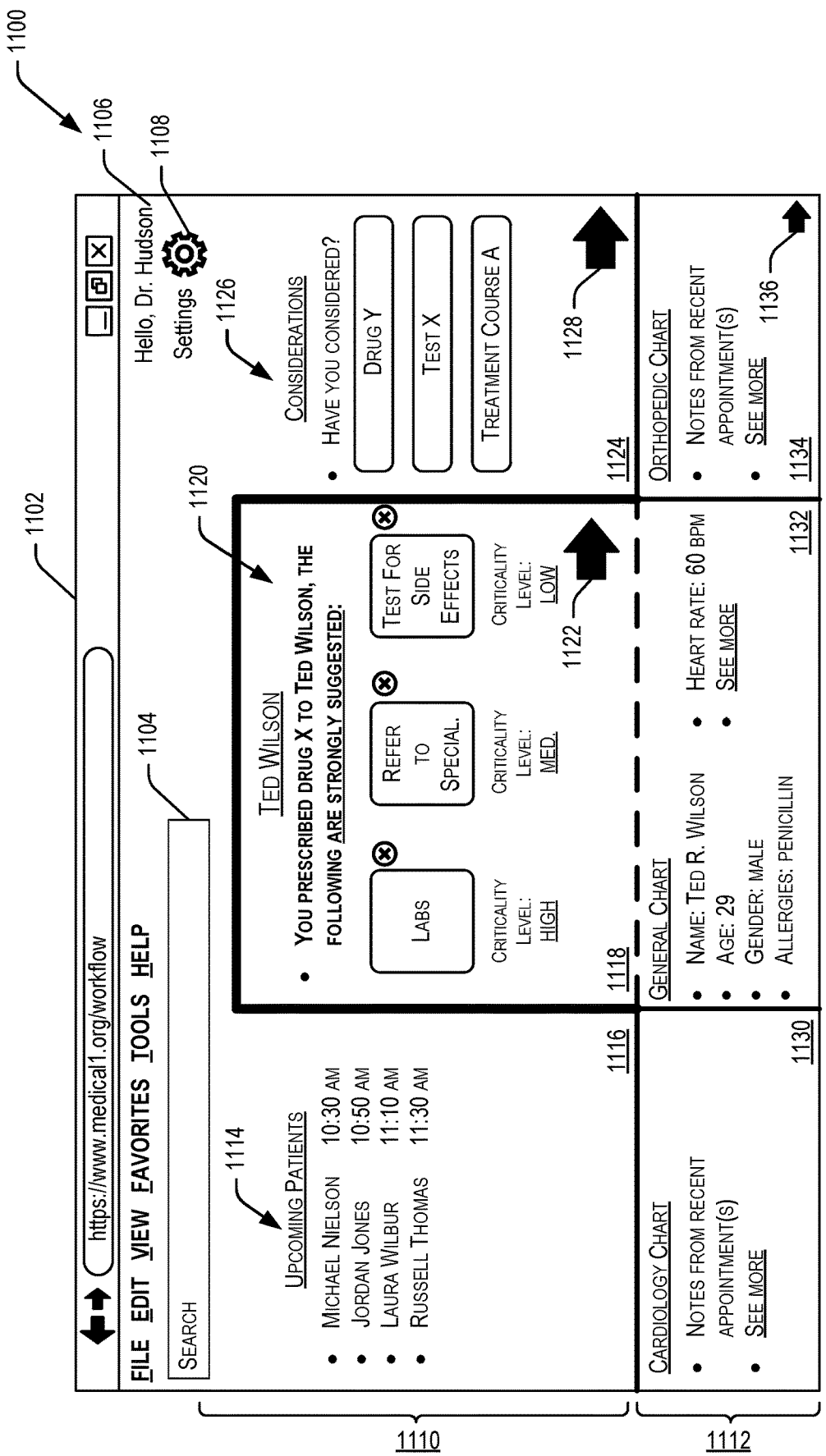
FIG. 11 is an example contextual user interface in which generated contextual suggestions may be provided to authorized users as described herein, according to at least one example.

Turning now to FIG. 11, a contextual medical user interface 1100 is shown in accordance with an embodiment of the invention. The contextual medical user interface 1100 is an example of the one of the user interfaces 906. Thus, in this example, the medical suggestion engine 902 provides medical decision support output to users via the contextual medical user interface 1100. The contextual medical user interface 1100 is illustrated as a webpage 1102. Thus, the contextual medical user interface 1100 in this example is a web interface. The webpage 1102 includes a search bar 1104 for searching within a medical provide network, the Internet, any other network, or within a database, data structure, or the like. The webpage 1102 also identifies Dr. Hudson 1106 as a medical care professional who has signed into the webpage 1102. Dr. Hudson 1106, or other user, may adjust the settings of how the webpage 1102 is configured and what information is presented by clicking on a settings icon 1108. Once Dr. Hudson 1106 adjusts the settings of the webpage 1102, the adjusted settings may be provided to the medical suggestion engine 902 to consider when making suggestions to Dr. Hudson 1106 via the webpage 1102.

The webpage 1102 includes workflow/suggestion area 1110 and patient chart area 1112. Within the workflow/suggestion area 1110 is presented patient list 1114 in area 1116. The patient list 1114 includes a list of patients that Dr. Hudson 1106 has on her schedule. The list includes "Ted Wilson" who Dr. Hudson 1106 is currently seeing. This may mean that Ted Wilson is being treated by Dr. Hudson 1106 or is waiting to be seen by Dr. Hudson 1106. The patient list 1114 also includes other patients that are on Dr. Hudson's 1106 schedule.

Adjacent to the area 1116, within the workflow/suggestion area 1110, and central to the webpage 1102 is area 1118. Within the area 1118 is presented medical suggestion information 1120. The medical suggestion information 1120 presented in the area 1118 includes medical suggestions that may be more critical than other medical suggestions. In other words, because the medical suggestion information 1120 is presented prominently in the center of the webpage 1102 (i.e., in the area 1118), Dr. Hudson 1106 may understand that the information presented here is important. In some examples, the medical suggestion engine 902 determines which medical suggestions should be presented based on a course of treatment. In this example, the medical suggestion information 1120 includes a sentence describing a course of treatment (i.e., "You prescribed drug X to Ted Wilson, the following are strongly suggested:") and a variety of medical tasks (i.e., "Labs" "Refer to Specialist," and "Test for Side of Effects") related to the course of treatment identified above. Clicking on a button that includes one of medical tasks (e.g., "Labs") may prompt the populator engine 1002 to identify and populate the appropriate forms for that medical task. In some examples, clicking the button provides additional information (e.g., medical journals, uses cases, availability, etc.) about the particular medical task. Each of the medical tasks include a criticality level as it relates to the course of treatment. For example, the medical task Labs includes a "high" criticality level. Because this information is presented to Dr. Hudson 1106, she can make an informed decision of whether to take the suggestion based on the context in which the suggestion is offered. In some examples, the medical suggestion information 118, including any medical suggestions described herein, may be determined and selectively presented based on the geographic location of the patient and/or the medical care professional (e.g., Dr. Hudson 1106).

Each of the medical tasks also includes an option to close out the suggestions. In some examples, this is considered an override of the suggestion and may be tracked by the medical suggestion monitor engine 920 for Dr. Hudson 1106, for the suggestion, for the course of treatment, and the like to learn how the suggestions are being considered. Additionally, Dr. Hudson 1106 can click arrow 1122 to reveal more suggestions relating to the identified course of treatment. In some examples, clicking the arrow 1122 may reveal other suggestions for other courses of treatment.

Adjacent to the area 1118 and within the workflow/suggestion area 1110 is area 1124. Within the area 1124 is presented medical consideration information 1126. The medical consideration information 1126 presented in the area 1124 includes medical considerations that may be less critical than the medical suggestions presented in the area 1118. It may be apparent that these medical considerations are less critical because they are presented off-center from the webpage 1102. The medical consideration information 1126 may include medical tasks related to the course of treatment or unrelated to the course of treatment. In some examples, the medical consideration information 1126 includes items that other doctors have considered when treating a patient similar (e.g., similar diagnosis, medical history, age, etc.) to Ted Wilson. Clicking on a button that includes one of medical tasks (e.g., "Drug Y") may prompt the populator engine 1002 to identify and populate the appropriate forms for that medical task. In some examples, clicking the button provides additional information (e.g., medical journal, uses cases, availability, etc.) about the particular medical task. Similar to the area 1118, the area 1124 includes arrow 1128. Clicking the arrow 1128 may reveal other medical considerations.

Below the workflow/suggestion area 1110 and within the patient chart area 1112 are areas 1130, 1132, and 1134. Generally, within the patient chart area 1112 is presented medical-related information from a medical record associated with Ted Wilson. In some examples, the medical record has been developed by different medical care professionals and may be organized according to specialty. Thus, within the area 1132 is presented general chart information. This information is associated with Ted Wilson, but general in the sense that almost any medical care professional would consider such information while treating Ted Wilson. To the left of the area 1132 is the area 1130. Within the area 1130 is presented cardiology chart information. This information also pertains to Ted Wilson, but may include certain entries that are specific for treatment by a cardiologist. Similarly, the area 1134 includes orthopedic chart information. In some examples, Dr. Hudson 1106 organizes the arrangement of information within the patient chart area 1112 by adjusting one or more settings associated with the contextual medical user interface 1100. In some examples, more or less chart information may be presented. By clicking arrow 1136, more types of chart information may be presented (e.g., neurology, oncology, etc.). In some examples, each of the areas 1130, 1132, and 1134 include a "see more" line. By clicking "see more," the contextual medical user interface 1100 is adjusted and more information is presented pertaining to the type of chart information. In some examples, any of the text on the webpage 1102 may be hyperlinked to present other content related to the linked text.

Figure 12:
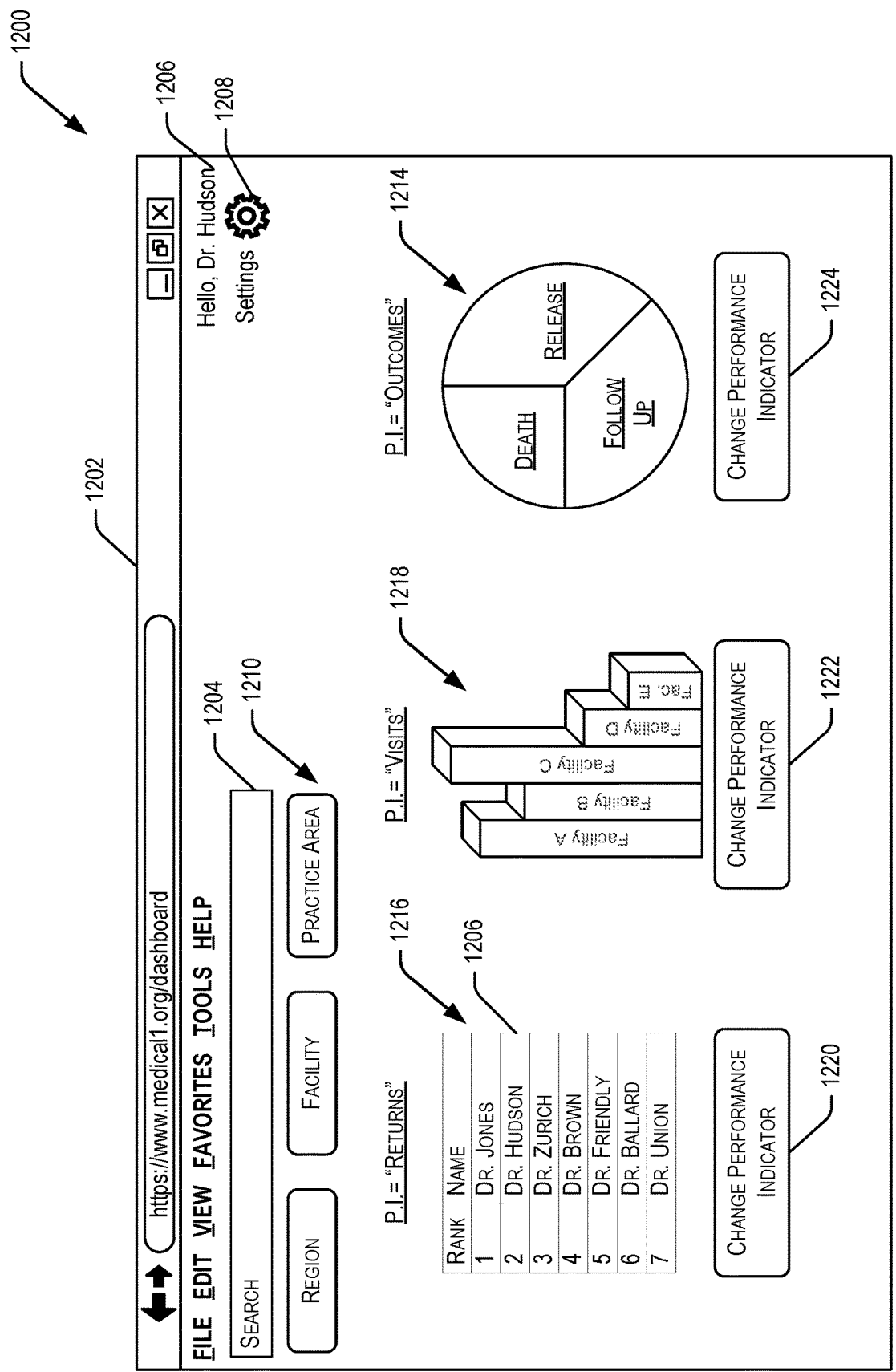
FIG. 12 is an example contextual user interface in which metrics related to authorized users may be presented and accessed as described herein, according to at least one example.

Turning now to FIG. 12, a medical analytics dashboard 1200 is shown in accordance with an embodiment of the invention. The medical analytics dashboard 1200 may be presented on one of the user interfaces 906. In some examples, the medical analytics dashboard 1200 is included as part of the contextual user interface 1100. The medical analytics dashboard 1200 is illustrated as a webpage 1202. The webpage 1202 includes a search bar 1204 for searching within a medical provide network, the Internet, any other network, or within a database, data structure, or the like. This may include searching medical analytics data, performance indicators, and the like. The webpage 1202 also identifies Dr. Hudson 1206 as a medical care professional who has signed into the webpage 1202. Dr. Hudson 1206, or other user, may adjust the settings of how the webpage 1202 is configured and what information is presented by clicking on a settings icon 1208. The webpage 1202 includes one or more filter criteria 1210 and one or more updateable graphical representations 1212. Clicking on one of the filter criteria 1210 may adjust what medical analytics data is presented by the updateable graphical representations 1212.

In some examples, the updateable graphical representations 1212 are presented as graphs, tables, or the like (e.g., in the form of application widgets) and organized based on medical care professional such as Dr. Hudson 1206. For example, for a particular medical performance indicator (e.g., "Outcomes"), the medical analytics data relating to this indicator is organized in a pie chart 1214 and presented in a way that informs Dr. Hudson 1206 of her own performance. The medical analytics data may also be presented in a way that compares medical care professionals according to the medical performance indicators. For example, for a particular medical performance indicator (e.g., "Returns"), the medical analytics data relating to this indicator is organized as a table 1216. Within the table 1216 is a ranking of medical care professionals, showing Dr. Hudson 1206 in the second position. The medical analytics data may also be presented in a way that compares medical care facilities according to the medical performance indicators. For example, for a particular medical performance indicator (e.g., "Visits"), the medical analytics data relating to this indicator is organized as a bar graph 1218. Within the bar graph 1218 is a comparison of medical care facilities. In some examples, such a comparison may be relevant to Dr. Hudson 1206 because Dr. Hudson 1206 practices at one of the facilities. Below each of the table 1216, the bar graph 1218, and the pie chart 1214 is a button (i.e., buttons 1220-1224) that can be selected to change the performance indicator. For example, selecting the button 1220 enables Dr. Hudson 1206 to change the performance indicator "Returns" to a different performance indicator (e.g., "Visits"). If done so, the table 1216 will be populated with medical analytics data pertaining to the indicator Visits.

Figure 13:
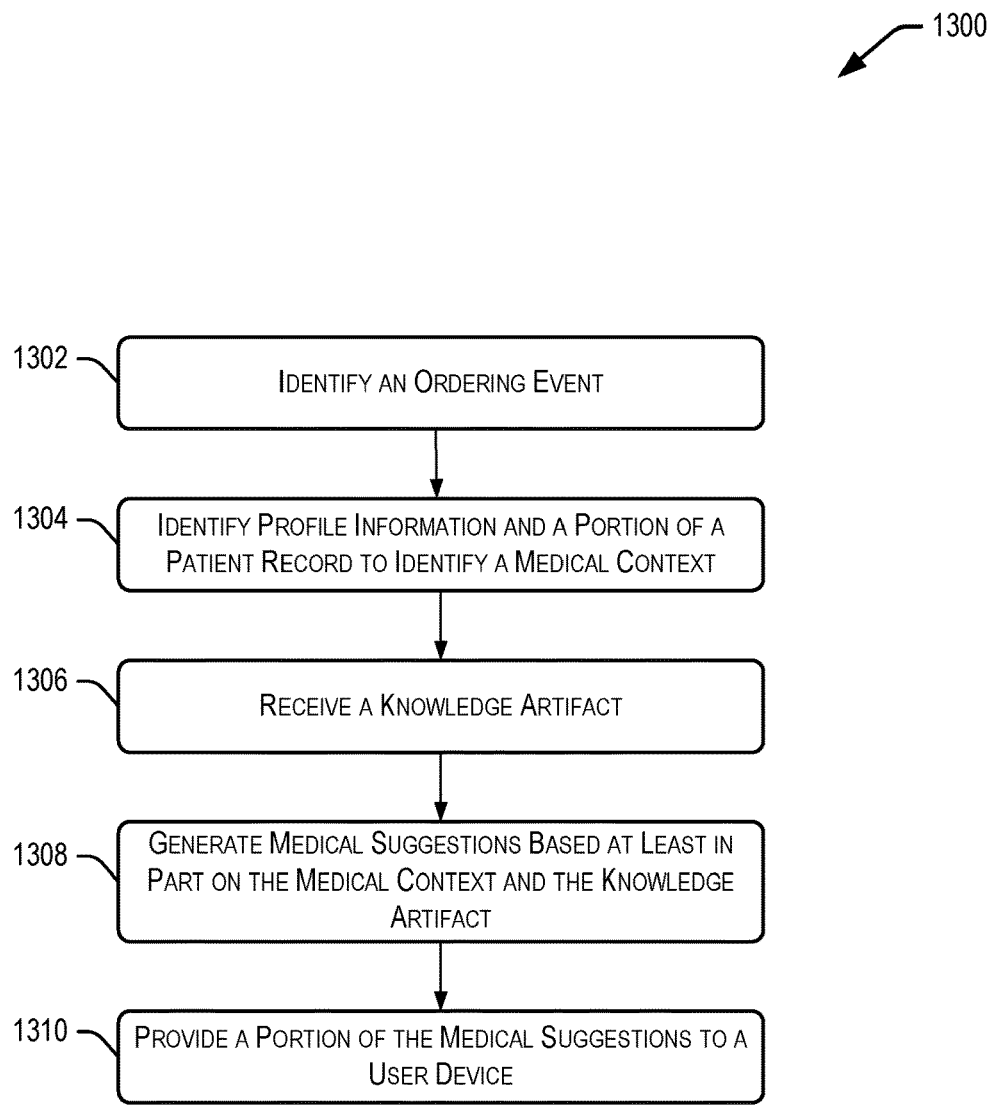
FIG. 13 is a flow diagram depicting example acts for implementing techniques relating to generating contextual suggestions and providing contextual suggestions to authorized users as described herein, according to at least one example.

FIG. 13 illustrates a flowchart of a process 1300 for generating a medical suggestion according to an embodiment of the invention. Some or all of the process 1300 (or any other processes described herein, or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The process 1300 begins at block 1302 by identifying an ordering event. The ordering event may correspond to a care scenario for a patient of a medical care professional. The ordering event may correspond to a decision point, an escalation event, and/or a communication event. The care scenario identifies details about the patient's care. For example, the care scenario may indicate a diagnosis, a treatment plan, a purpose for a visit to see the medical care professional, and the like. In some examples, the ordering event is any action initiated on behalf of the patient that affects the care scenario and/or medical care of the patient. For example, the ordering event may include the medical care professional (or other medical care professional) ordering a test for the patient, scheduling an appointment for the patient, reviewing a medical chart of the patient, prescribing a drug for the patient, providing a referral to the patient, requesting a consultation on behalf of the patient, recording a diagnosis of the patient in a medical record associated with the patient, and other similar event corresponding to the care scenario of the patient.

At 1304, the process 1300 identifies profile information and a portion of a patient record to identify a medical context. The profile information may correspond to the medical care professional and may include a medical profile. The medical profile includes details about the medical care professional, e.g., area of practice, geographic location, preferences, and the like. The medical patient record includes medical-related information that describes the patient and his or her medical history. Because the medical context is based on the profile information and the medical patient record, the medical context describes a context in which the medical care professional provides medical care to the patient. For example, the medical context may also be based on the care scenario of the patient. Thus, the medical context may describe who the patient is (i.e., the medical patient record), what diagnosis the patient has (i.e., the care scenario and/or the medical patient record), and who (i.e., the medical care professional) is treating the patient.

At 1306, the process 1300 receives a knowledge artifact. The knowledge artifact may be determined based on medical-related information previously collected for other patients. The knowledge artifact may be included in a list of knowledge artifacts that may include internal knowledge artifacts, external knowledge artifacts, and a combination of internal and external knowledge artifacts. An knowledge artifact is an organization of medical-related information in a manner that is readable by a medical suggestion engine to implement techniques described herein.

At 1308, the process 1300 generates medical suggestions based on the medical context and the knowledge artifact. The medical suggestions may correspond to one or more possible courses of treatment for the care scenario of the patient. For example, the medical suggestions may include suggestions that, based on the medical context for a patient and a knowledge artifact collected for similar patients, the patient should be removed from a drug, be administered a test, or some other similar course of treatment. The medical suggestions may indicate a mapping of courses of treatment to outcomes based on the courses of treatment. The more successful courses of treatment may have a greater weighting. The medical suggestions may also be provided in a list of medical suggestions that may rank medical suggestions based on criticality. In some examples, the medical suggestions may be generated in a manner that provide the best possible outcomes in the most cost efficient manner. For example, when the medical suggestion relates to diagnostic testing, the medical suggestions may be generated based on the cost of available and applicable diagnostic testing.

At 1310, the process 1300 provides a portion of the medical suggestions to a user device. This may include providing one or more medical suggestions for presentation on a user interface of a user device. The user device may be associated with the medical care professional. Thus, the medical care professional that is treating the patient may receive one or more medical suggestions pertaining to the treatment of the patient. The medical suggestions may be tailored to the particular medical care professional by considering his or her specialty, preferences, patterns of treatment and the like, and be tailored to the patient by considering his or her medical history and current care scenario.

Figure 14:
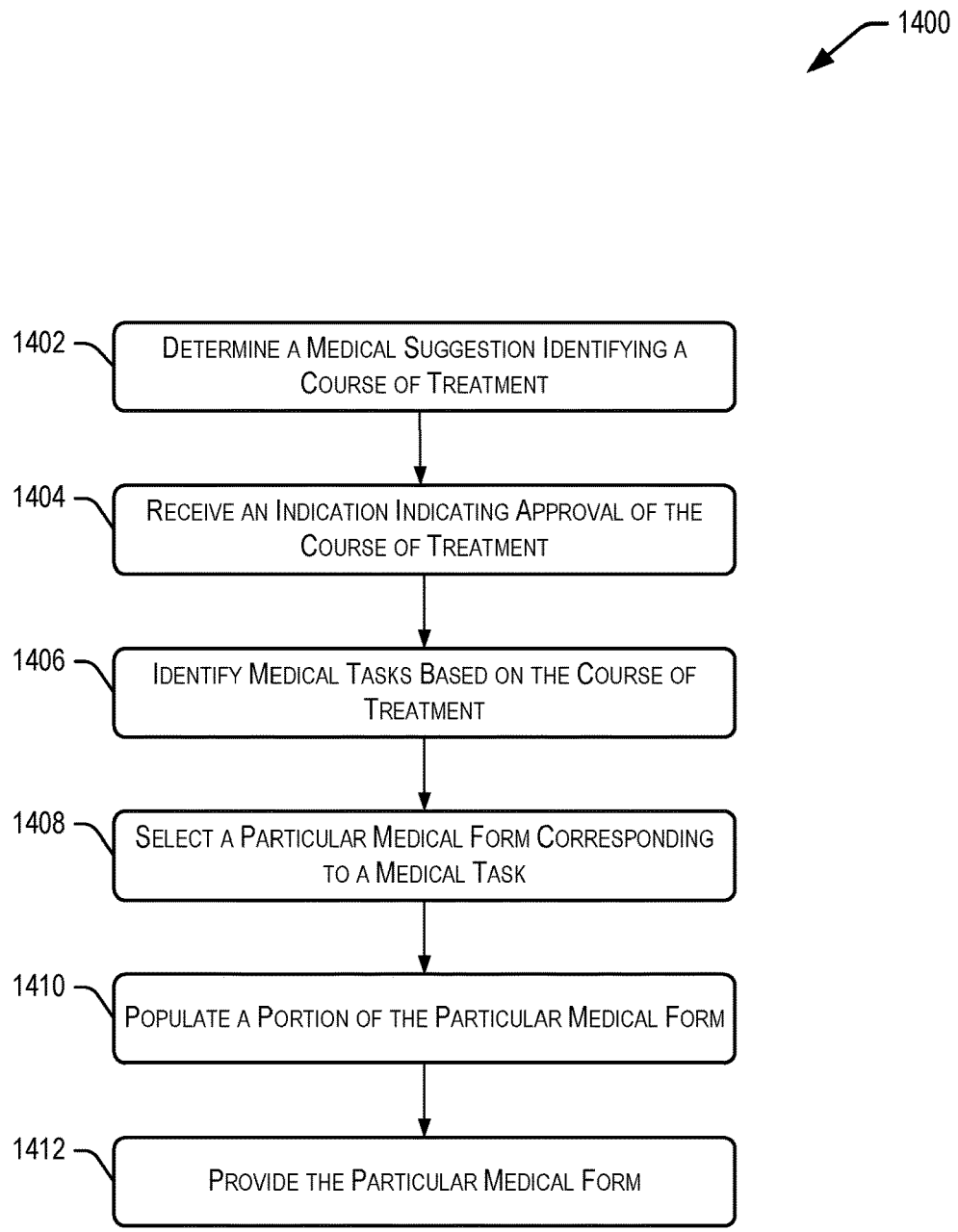
FIG. 14 is a flow diagram depicting example acts for implementing techniques relating to generating contextual suggestions and providing contextual suggestions to authorized users as described herein, according to at least one example.

FIG. 14 illustrates a flowchart of a process 1400 for populating a medical form based on a medical suggestion according to an embodiment of the invention. The process 1400 begins at block 1402 by determining a medical suggestion identifying a course of treatment. The medical suggestion may be determined based on a knowledge artifact as described herein. The course of treatment may be particular to a patient and/or may be general for any patient sharing similar characteristics as identified by the knowledge artifact. The medical suggestion may also depend on a medical context for the treatment of the patient.

At 1404, the process 1400 receives an indication indicating approval of the course of treatment. The indication may be received from the medical care professional. The indication may indicate approval of the course of treatment identified by the medical suggestion. This may involve the medical care professional selecting a course of treatment via a user interface after the suggestion has been made to the medical care professional and presented at the user interface. In some examples, the medical care professional adjusts the course of treatment prior to indicating his or her approval. Thus, in some examples, the approved course of treatment may be a revised and/or adjusted course of treatment. In some examples, the medical care professional inputs his or her own course of treatment.

At 1406, the process 1400 identifies medical tasks based on the course of treatment. At least some of the medical tasks may involve submission of a medical form as a precondition to performance of the medical task. For example, prior to fulfilling a prescription for a drug (e.g., a medical task) to treat a cold (e.g., a course of treatment), a prescription (e.g., a form) must be filled out and signed by the medical care professional (e.g., a precondition). Other forms for other medical tasks may also be required prior to performance of the other medical tasks.

At 1408, the process 1400 selects a particular medical form corresponding to the medical task. The selecting may be based on a user input indicating the particular medical form and/or may be performed programmatically depending on the course of treatment for the patient, preferences of the medical care professional, and the like. The particular medical form may be selected from a list of medical forms pertaining to the same medical task. For example, for a referral to orthopedic surgeon A, referral from A may be required, for a referral to orthopedic surgeon B, a referral from B may be required, and so forth. The particular medical form may be selected from a list of medical forms pertaining to different medical tasks. For example, for a referral to orthopedic surgeon A, referral form A may be required, for a lab test B, a lab test request form B may be required, and so forth.

At 1410, the process 1400 populates a portion of the particular medical form. This may include populating the medical form with patient information from a patient record of the patient or profile information of the medical care professional. Populating the portion of the particular medical form may also include populating a portion of the fields of the particular medical form.

At 1412, the process 1400 provides the particular medical form. Providing the particular medical form may involve providing the form to a different medical care professional for performance of the medical task associated with the medical task.

Figure 15:
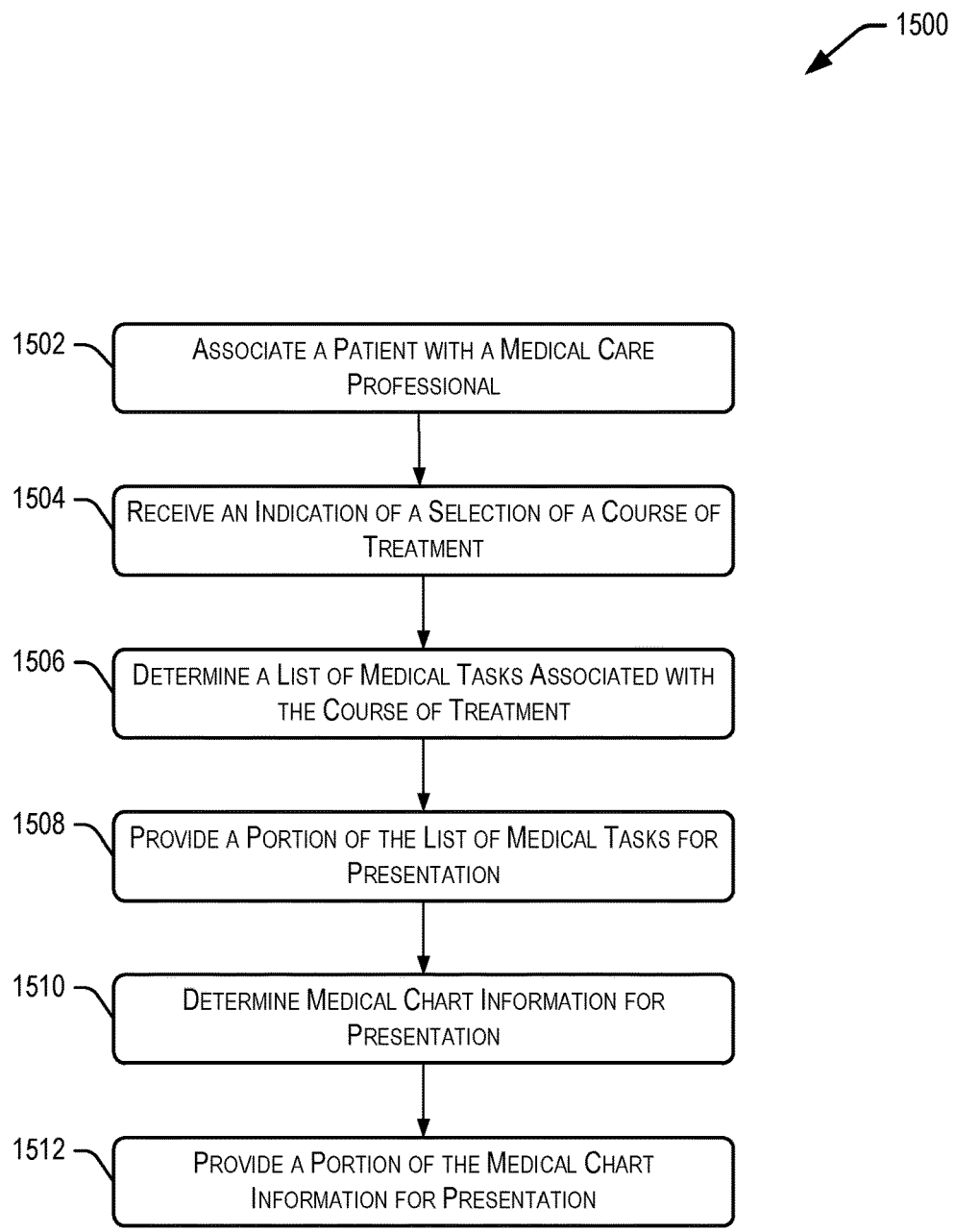
FIG. 15 is a flow diagram depicting example acts for implementing techniques relating to generating contextual suggestions and providing contextual suggestions to authorized users as described herein, according to at least one example.

FIG. 15 illustrates a flowchart of a process 1500 for providing medical tasks associated with a patient for presentation according to an embodiment of the invention. The process 1500 begins at block 1502 by associating a patient with a medical care professional. The medical care professional may belong to a medical provider network. Associating the patient with the medical care professional may involve identifying in a database of the medical care provider network that the patient has implicitly or explicitly requested treatment from the medical care professional.

At 1504, the process 1500 receives an indication of a selection of a course of treatment. The medical care professional may select the course of treatment by selecting the course of treatment from a list of possible courses of treatment based on the care scenario. In some examples, the course of treatment may be determined by evaluating a patient medical record and/or a profile for the medical care professional.

At 1506, the process 1500 determines a list of medical tasks associated with the course of treatment. The list of medical tasks may comprise a list of medical suggestions. The list of medical tasks may be determined based on profile information for the medical care professional and a portion of the patient record of the patient.

At 1508, the process 1500 provides a portion of the list of medical tasks for presentation. In some examples, the portion of the list of medical tasks is provided for presentation in a primary area of a user interface of a user device associated with the medical care professional. The portion of the list of medical tasks may include one or more medical tasks. The one or more medical tasks may be weighted, prioritized, and/or ranked in a manner that accounts for medical criticality of the medical task, acceptance of the task by others, preferences of the medical care professional, and other factors. The one or more medical tasks may be presented based on state of the patient (e.g., the patient is a stroke patient, so present medical task A now) or based on time (e.g., the patient just became a patient of the medical care professional, so present medical task B now). At 1508, the process 1500 also determines how to present the one or more medical tasks in a manner that emphasizes the criticality of certain medical tasks over others. More critical medical tasks may be presented in a more invasive manner (e.g., centered on the user interface, including large font, bright colors, flashing, as a pop-up, require a click-through to close, and other similar techniques). Less critical tasks may be presented in a less invasive manner. Such less critical tasks may include considerations that the medical care professional should take in to account as a best practice (e.g., "When a patient is diagnosed with heart disease, other doctors request lab X be performed periodically, have you considered ordering lab X for the patient?"). For example, the rules to generate and present the less critical tasks may indicate prior practices of the medical care professional (e.g., "You typically prescribe drug X, would you like to prescribe drug X to this patient?").

In some examples, the one or more medical tasks may be overridden by the medical care professional. The number of overrides may be recorded for each recommended medical task. When an override rate exceeds a particular threshold, it may be flagged and provided to an authorized user for review. An excessive amount of overrides may indicate that the suggested medical task is not appropriate, is irrelevant, or that medical care professionals do not have a preference for the medical task. In some examples, the success rates for accepted medical tasks may be tracked and may be compared to the clinical result for the particular patient for which the medical task was performed. In this manner, the medical outcome for each suggested medical task can be tracked. In some examples, if the medical care professional accepts a suggested medical task from a first list, the techniques described herein may generate a second list of medical tasks. Thus, the selection of the suggested medical task may prompt the generation and presentation of other medical tasks. In some examples, this process may continue until there are no medical tasks to suggest. In some examples, which medical tasks are suggested depends on the geographic location where the patient is located. For example, in a first geographic area experiencing an outbreak of the flu, a first medical task may be suggested for the patient. However, for the same patient in a second geographic area (not experiencing an outbreak of the flu), a second medical task may be suggested for the patient. In this manner, the techniques described herein provide suggested medical tasks based on the context in which the medical care professional is practicing. This context is what makes the suggestions and other information meaningful.

At 1510, the process 1500 determines medical chart information for presentation. In some examples, the medical chart information is determined based on one or more settings and/or preferences provided by the medical care professional. The medical chart information may include general chart information that is relevant to all medical decisions and specialty chart information that may be organized according to specialty (e.g., orthopedics, oncology, neurology, etc.). A medical care professional may subscribe to receive specialty chart information and the general chart information as a data feed. In some examples, certain medical care professionals may be interested in viewing information for specialties outside of their general area of practice. This preference is accounted for in determining medical chart information.

At 1512, the process 1500 provides a portion of the medical chart information for presentation. This may include presenting medical chart information based on one or more settings and/or preferences provided by the medical care professional. The portion of the medical chart information is presented in a secondary area of the user interface in a manner that emphasizes the list of medical tasks presented in the primary area. The secondary area may be secondary because of where it is placed relative other areas and/or because of how the second area is laid out.

Figure 16:
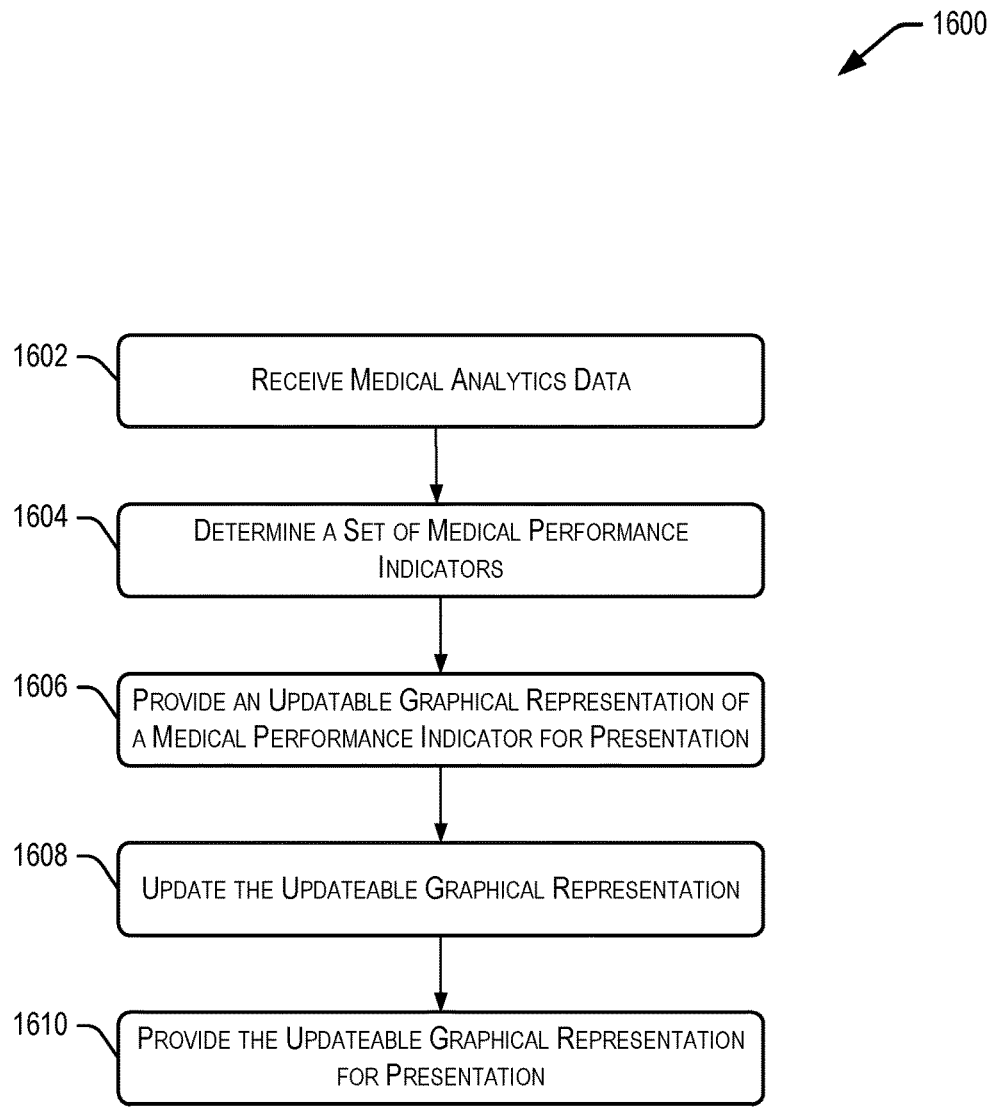
FIG. 16 is a flow diagram depicting example acts for implementing techniques relating to generating contextual suggestions and providing contextual suggestions to authorized users as described herein, according to at least one example.

FIG. 16 illustrates a flowchart of a process 1600 for providing medical performance indicators for presentation according to an embodiment of the invention. The process 1600 begins at block 1602 by receiving medical analytics data. In some examples, the medical analytics data is collected from at least one medical care facility including a plurality of medical care professionals. In some examples, the medical analytics data is collected from a plurality of medical care facilities extending throughout many geographic areas. In some examples, the medical analytics data is organized prior to being received at 1602.

At 1604, the process 1600 determines a set of medical performance indicators. In some examples, the set of medical performance indicators correspond to a medical care professional. The medical performance indicators may also be determined based on the medical analytics data. The medical performance indicators may include indicators that can be used to rate, evaluate, judge, or otherwise compare the medical care professional to a baseline or to other medical care professionals.

At 1606, the process 1600 provides an updateable graphical representation of the a medical performance indicator for presentation. The updateable graphical representation may be presented on a user interface of a user device associated with the medical care professional. The updatable graphical representation may be representative of a particular medical performance indicator. The updateable graphical representation may be updated periodically, in accordance with a rule, or in any other suitable manner to ensure that the updatable graphical representation represents current medical analytics data. Examples of the updatable graphical representation include bar graphs, tables, lists, pie charts, line graphs, Venn diagrams, and other methods of presenting medical analytics data.

At 1608, the process 1600 updates the updateable graphical representation. This may involve updating the updatable graphical representations in response to a change of a portion of the medical analytics data corresponding to the performance indicator. In some examples, the updatable graphical representation is updated in accordance with one or more rules, which may be user-defined and/or machine-defined.

At 1610, the process 1600 provides the updated graphical representation for presentation. In some examples, this may involve providing the updated graphical representation for presentation on the user interface of the user device.

Figure 17:
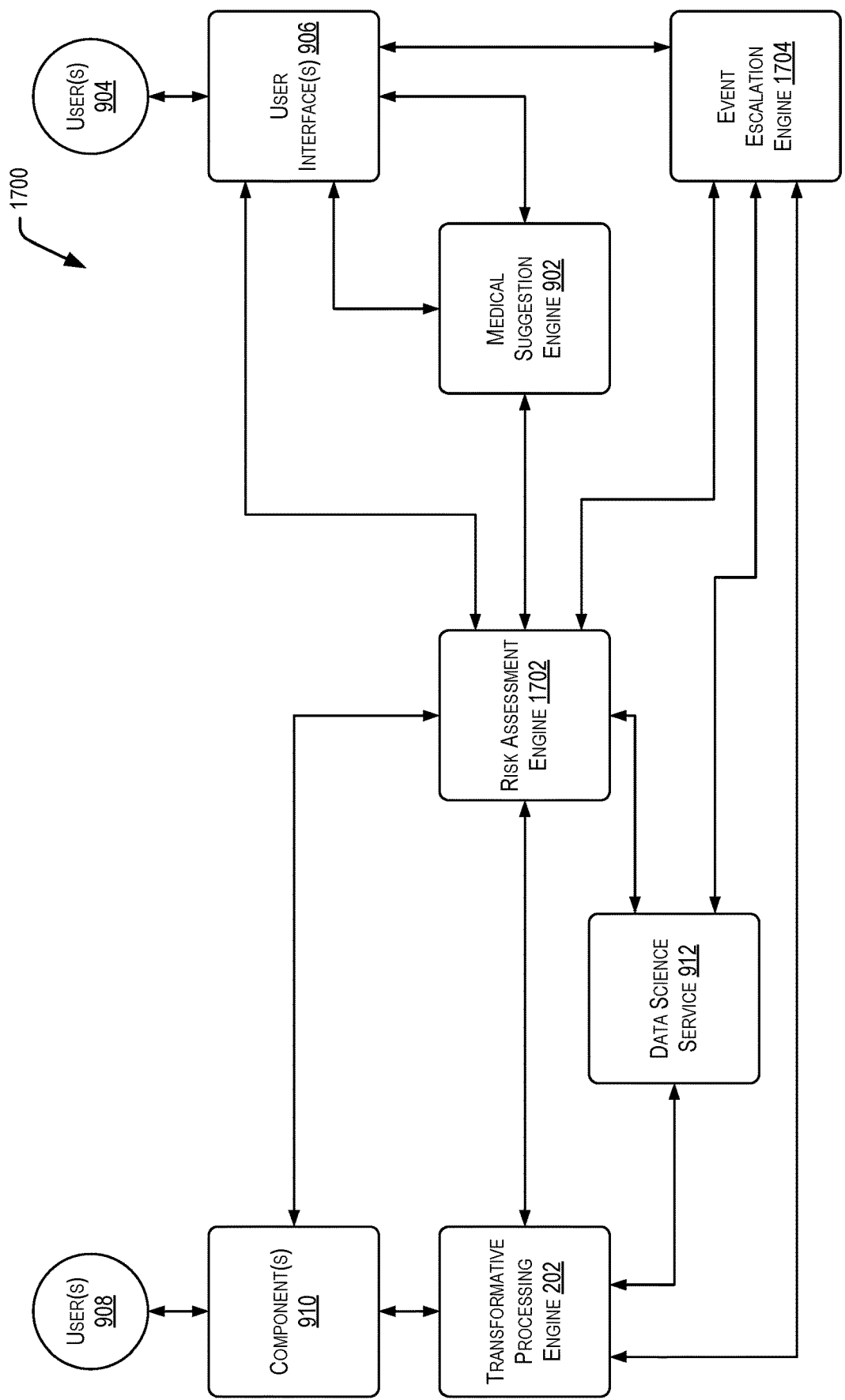
FIG. 17 is an example block diagram illustrating techniques relating to evaluating risk and generating a risk assessment for authorized users as described herein, according to at least one example.

Turning now to FIG. 17, a medical provider network 1700 is shown in accordance with an embodiment of the invention. The medical provider network 1700 may be implemented using at least some of the elements of the medical provider network 800. The medical provider network 1700 includes a risk assessment engine 1702 and an event escalation engine 1704, which are configured to implement the techniques described herein. For example, the risk assessment engine 1702 generates medical decision support output (e.g., risk assessments, medical predictions, deterioration status, and the like) that can be provided to the receiving users 904 via the one of more user interfaces 906. In order to generate the medical decision support output, the risk assessment engine 1702 receives and analyzes medical-related data. In this example, the medical-related data includes subjective data (e.g., doctor notes, on-call nurse notes, patient-prepared materials, transcriptions of medical notes, recordings (or transcriptions) of interactions between patients and medical care professionals and/or between patients and others (e.g., family members), notes regarding eating habits of a patient, notes regarding bathroom habits of the patient, prescription notes, discharge notes (e.g., emergency room discharge), notes regarding radiology and other tests, and other types of subject data) and objective data (e.g., orders, lab results, vital signs from chart, objective output from medical devices and/or medical systems, pharmacy orders, weather conditions, and other types of objective data). In some examples, the subjective data is unstructured data (e.g., letters, numbers, and symbols stored in an unknown format) and the objective data is structured data (e.g., letters, numbers, and symbols stored in a known format). However, the structured data may also include some subjective data and the unstructured data may include objective data. In some examples, the risk assessment engine 1702 and/or the event escalation engine 1704 are implemented as engines within the medical suggestion engine 902 as discussed with reference to FIG. 9.

The creation of such medical-related data begins with the generation users 908. The generation users 908 and the receiving users 904 may come from the same group of users and may be similar to the users that operate the components 410-418 and/or the users that operate the user devices 706-714. Accordingly, the generation users 908 interact with components 910 to generate medical-related data, and the receiving users 904 receive medical decision support output via the user interfaces 906. In some examples, the user interfaces 906 are implemented at one or more of the components 910. In other words, a particular component 910 can generate medical-related data and can also receive medical decision support output. The components 910 are examples of the components 410-418 discussed herein. Thus, in some examples, the components 910 automatically generate medical-related data without input by the generation users 908. For example, an automated process running on a particular component periodically outputs a report of current patients.

The medical-related data generated by the users 908 interacting with the components 910 is provided to the transformative processing engine 202 and the transformative processing engine 202 performs one or more operations on the medical-related data such as those discussed herein. In some examples, the transformative processing engine 202 may be configured to collect clinical information that supports clinical trials.

Human scientists and/or automated processes of the data science service 912 access the medical-related data stored by the transformative processing engine 202 and attempt to give the data medically-relevant meaning as described herein.

The transformative processing engine 202 may provide or make available certain types of and/or classes of medical-related data to the risk assessment engine 1702. As described herein, the risk assessment engine 1702 generates a particular class of medical decision support output. For example, the risk assessment engine 1702 generates risk assessments (e.g., medical predictions and deterioration assessments) based on data accessed from the transformative processing engine 202. To this end, the risk assessment engine 1702 includes one or more rule sets that can be evaluated to determine whether certain input information (e.g., medical-related data) triggers one or more outputs. For example, the risk assessment engine 1702 may use real-time data received from the transformative processing engine 202 and/or from one of the components 910 to determine whether a patient has early symptoms of sepsis. In some examples, the risk assessment engine 1702 identifies such symptoms earlier than a reasonable medical care professional would be able to. This may be because the risk assessment engine 1702 is configured to evaluate, in real-time, objective and subjective medical-related data in order to determine one or more risk assessments. Even when the medical-related data is not real-time data, the risk assessment engine 1702 nevertheless may generate a risk assessment earlier than a medical care professional because the risk assessment engine 1702 is configured to evaluate very large data sets of medical-related data, and to draw conclusions and/or inferences from the data. In some examples, once the risk assessment engine 1702 draws a conclusion from the medical-related data, this conclusion can be included in a risk assessment, which can be provided to the users 904. In some examples, the risk assessment includes a diagnosis of a particular health condition. In some examples, the risk assessment includes a notification that a patient with an existing condition is deteriorating. The risk assessment can also be provided to the transformative processing engine 202 where it can be verified by a medical professional or otherwise to determine whether the risk assessment, including the diagnosis and deterioration assessment, were correct.

In some examples, at least a portion of the medical-related data used by the risk assessment engine 1702 is received from the data science service 912 in the form of one or more knowledge artifacts. The one or more knowledge artifacts are characterized as objective medical-related data or subjective medical-related data depending on the type and class of the artifacts.

Once a risk assessment or other type of medical decision support output has been generated by the risk assessment engine 1702, the risk assessment is provided directly to the user interface 906 to be consumed by one of the receiving users 904. This includes, for example, providing the risk assessment (or a communication including at least a portion of the risk assessment) into an existing clinical workflow. In some examples, the risk assessment is provided to a nurses' station as a notification for an on-call nurse to address. The risk assessment indicates the patient, a health disorder associated with the patient (whether current or possible), the patient's risk as it relates to the health disorder, and any other suitable information.

In some examples, the risk assessment or other medical decision support output is provided to the medical suggestion engine 902, and the medical suggestion engine 902 generates a medical suggestion based on the risk assessment. The medical suggestion engine 902 then provides the medical suggestion, including the risk assessment, to the receiving users 904 via the user interfaces 906 as described herein. Thus, the medical suggestion engine 902 can use the risk assessment as input as described herein.

The risk assessment engine 1702 can also provide the risk assessment or other medical decision support output to the event escalation engine 1704. As described herein, the event escalation engine 1704 is configured to detect occurrence of a notification event (e.g., a change in a patient's condition, which may be evidenced by the risk assessment), identify a recipient and a notification based on a directory of recipients, and provide the notification to a first recipient based on an escalation tree. Thus, the event escalation engine 1704 can determine whether the risk assessment is the type that should be sent out, what of the substance of the risk assessment should be sent out, to whom the risk assessment should first be sent, and if that person is non-responsive or a communication including the risk assessment does not reach its destination, to whom the risk assessment should next be sent.

The event escalation engine 1704 is also configured to identify the occurrence of events other than receiving a risk assessment. For example, the event escalation engine 1704 can access knowledge artifacts from the data science service 912, objective medical-related data from the transformative processing engine 202, and/or subjective medical-related data from the transformative processing engine 202 in order to identify the occurrence of an event. To this end, the event escalation engine 1704 is configured to analyze the accessed medical-related data in order to identify certain events, which are defined by rule sets. For example, a rule set may indicate which conditions trigger "occurrence" of an event. For example, when the event escalation engine 1704 receives medical-related data indicating that a patient is checking into a hospital, the event escalation engine 1704 generates and sends a notification to the patient's primary care doctor. The condition of the patient checking into the hospital was sufficient, in this example, to constitute the occurrence of an event, and therefore cause a notification to be generated.

If the primary care doctor does not respond to the notification within a set period of time (e.g., 2 hours) or if the event escalation engine 1704 does not receive verification of delivery of the notification to the primary care doctor (e.g., a message delivery confirmation), the event escalation engine 1704 escalates the notification to a second recipient or system based on an escalation tree. In some examples, the second recipient may be an individual or system that is better suited to respond to the notification, which may be specifically identified (e.g., "Dr. Wilson Jones" who covers for the primary care doctor when he is out of the office) or generically identified (e.g., "another primary care doctor" who covers for the primary care doctor when he is out of the office). For example, when the primary care doctor is out of office (and cannot therefore receive notifications), the event escalation engine 1704 identifies, from the escalation tree, a second doctor that covers for the primary care doctor when he is out of the office.

Figure 18:
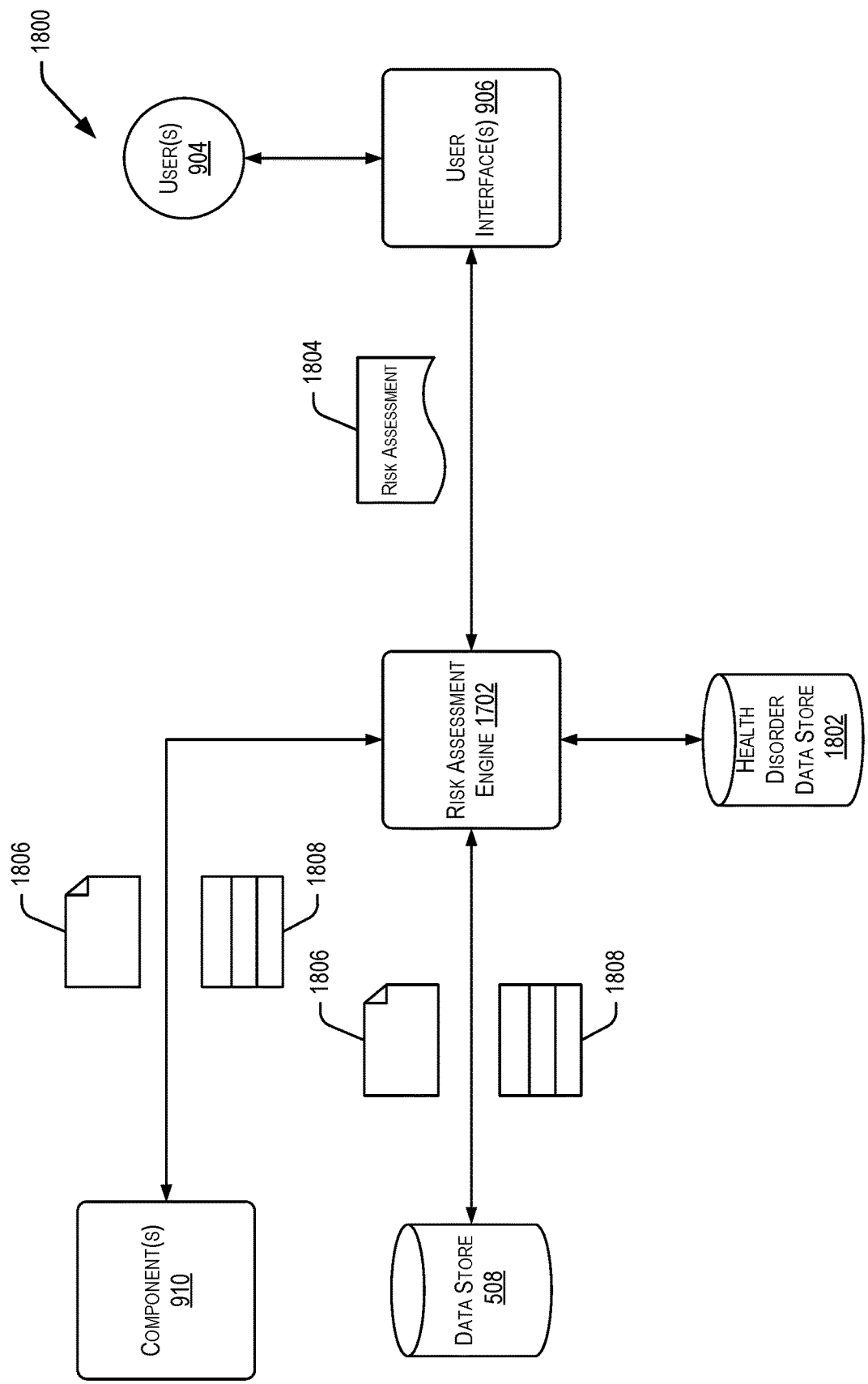
FIG. 18 is an example block diagram illustrating techniques relating to evaluating risk and generating a risk assessment for authorized users as described herein, according to at least one example.

Turning now to FIG. 18, a medical provider network 1800 is shown in accordance with an embodiment of the invention. The medical provider network 1800 includes the risk assessment engine 1702 in communication with the data store 508 (associated with the transformative processing engine 202), the user interfaces 906, and a health disorder data store 1802. As discussed herein, within the data store 508 is stored medical-related data, which is searchable and accessible by the risk assessment engine 1702. The risk assessment engine 1702 is configured to access medical-related data from the data store 508 and/or from the components 910 in order to generate one or more risk assessments 1804. In particular, the risk assessment engine 1702 accesses unstructured data 1806 and/or structured data 1808 from the data store 508 and/or the components 910. Thus, in some examples, portions of the unstructured data 1806 and/or portions of the structured data 1808 are received in real-time from the components 910 that generated and/or aggregated the unstructured data 1806 and/or the structured data 1808. In some examples, this may enable the risk assessment engine 1702 to receive medical-related data in real-time (e.g., at the network speed it takes for data to transfer from a component to the risk assessment engine 1702).

In some examples, the unstructured data 1806 is considered unstructured because the risk assessment engine 1702 cannot recognize the organization of the data. Thus, in order to derive meaningful information from the unstructured data 1806, the risk assessment engine 1702 uses one or more natural language processing techniques to analyze the unstructured data 1806. Using these techniques, the risk assessment engine 1702 identifies not only what words, symbols, and letters are included in the unstructured data 1806, but also parses the unstructured data 1806 to identify meaning, tone, sentiment, humor, sarcasm, and other forms of speech present in the unstructured data 1806. Examples of the unstructured data 1806 include: prose text written by a nurse or doctor that is included in a chart note of a patient or other data structure, graphical depictions prepared by a nurse or doctor that is included in a chart note of a patient or other data structure, prose text or graphical depictions prepared by a patient, family member, or other loved one of the patient that are related to the patient's care, and any other suitable unstructured data that can be analyzed by the risk assessment engine 1702.

In some examples, the structured data 1808 is considered structured because the risk assessment engine 1702 recognizes the organization of the data. This may be because the structured data 1808 is organized in a format that the risk assessment engine 1702 can immediately interpret. For example, a message that includes the structured data 1808 may have a fixed number of data fields (e.g., three) separated by commas, and may also include a text string in a header of the message that identifies what type of structured data 1808 is included in the message. Deriving meaningful information from the structured data 1808, in some examples, is performed relatively quickly compared to the unstructured data 1806. This is because when parsing the structured data 1808, the risk assessment engine 1702 essentially knows the format of the structured data 1808, which enables the risk assessment engine 1702 to determine what data is important and what can be disregarded. Thus, the structured data 1808 may include electronic data that includes discrete data elements organized in a standardized manner. Examples of the structured data 1808 include: results of lab tests, narrative text that is encoded with discrete data elements, results of customary vital-sign tests, and any other suitable structured data that can be analyzed by the risk assessment engine 1702.

As part of generating the risk assessment 1804, the risk assessment engine 1702 accesses the health disorder data store 1802. In some examples, the health disorder data store 1802 includes one or more health disorders for which the risk assessment 1804 can be generated and that are associated with one or more symptoms. The one or more health disorders include, for example, medical diseases, medical conditions, and medical disorders, whether mental or physical, for which the risk assessment 1804 can be generated. The one or more symptoms are associated with their respective disorders and retained in the health disorder data store 1802. Thus, for each health disorder, there are one or more symptoms which are typically associated with the health disorder. In some examples, the presence of a symptom is a necessary condition of the health disorder. In some examples, the presence of a symptom is a sufficient condition of the health disorder. In some examples, however, the presence of certain sets of symptoms in the absence of others, may be a necessary condition of the health disorder, a sufficient condition of the health disorder, or have no bearing on the determination of the health disorder. In some examples, a patient may already be diagnosed with one of the one or more health disorders in the health disorder data store 1802. In this example, the risk assessment engine 1804 may evaluate the symptoms of the known health disorder in order to determine whether the patient's condition, with respect to the known health disorder, is deteriorating.

A symptom rule is associated with each of the symptoms of the health disorder in order to determine whether the medical-related data indicates that the patient has the symptom. Thus, the symptom rule indicates what data should be present to identify that the patient has the symptom. Each symptom rule may also include a weighting relative to the health disorder and a numerical score for each health disorder. For example, if symptom X is present, the patient may be 100% likely to have the health disorder or 50% likely to have the health disorder. The weighting also takes into account the known details about the patient (e.g., medical history, stats, and the like). The scoring for each symptom may be used to quantify likelihoods that the patient has certain health disorders. For example, a certain health disorder may be included in a risk assessment, which may or may not be a diagnosis, when a numerical score meets or exceeds 90 points. Thus, 90 points may be a maximum threshold. In this example, symptoms X and Y are determined to be present and they have a numerical scores of 30 and 60, respectively. Thus, a total score of 90 has been determined. Based on this, the risk assessment engine 1702 can include the certain health disorder in the risk assessment 1804.

Because the symptom rules are associated with health disorders, the risk assessment engine 1702 evaluates the medical-related data (i.e., the unstructured data 1806 and/or the structured data 1808) on a medical-condition basis in order to generate the risk assessment 1804. In some examples, the risk assessment engine 1702 initially evaluates those health disorders that the patient presents a higher risk for, then evaluates other less critical health disorders. The risk assessment engine 1702 may analyze one or more health disorders simultaneously (e.g., in parallel) or in serial. In any event, the evaluation may be structured such that classes of health disorders may be eliminated or not even evaluated when elimination or presence of a certain health disorder affects others (e.g., rules them out of consideration).

Thus, the risk assessment 1804 is generated on a per health disorder basis. In some examples, the risk assessment 1804 includes a listing of all the health disorders that were analyzed, including a numerical score for each compared to a threshold score for each. In some examples, the numerical score can be used to determine a likelihood that the patient has the disorder. Whether as a straight numerical score or a likelihood, an operator or medical care professional can evaluate the list and decide whether further follow up with the patient would be helpful.

In some examples, the risk assessment 1804 includes a minimum amount of information to enable one of the receiving users 904 (e.g., a medical care professional) to see who the patient is (e.g., John Doe), what health disorder may be present (e.g., sepsis), a summary of what prompted the risk assessment 1804 (e.g., the structured data 1808 and the unstructured data 1806 and/or the symptoms that the risk assessment engine 1702 identified), a criticality score for the health disorder (e.g., based on the health disorder and the symptoms, how critical is the risk assessment), which may correspond to a range of scores, progression rate (e.g., how the health disorder is likely to progress), and any other suitable information.

In some examples, the risk assessment 1804 is provided to the receiving users 904 via the user interfaces 906. The receiving users 904 interact with the risk assessment engine 1702 via the user interfaces 906. Such interactions include, for example, requesting additional information relating to the risk assessment 1804, updating information within the health disorder data store 1802, and any other suitable interaction.

Figure 19:
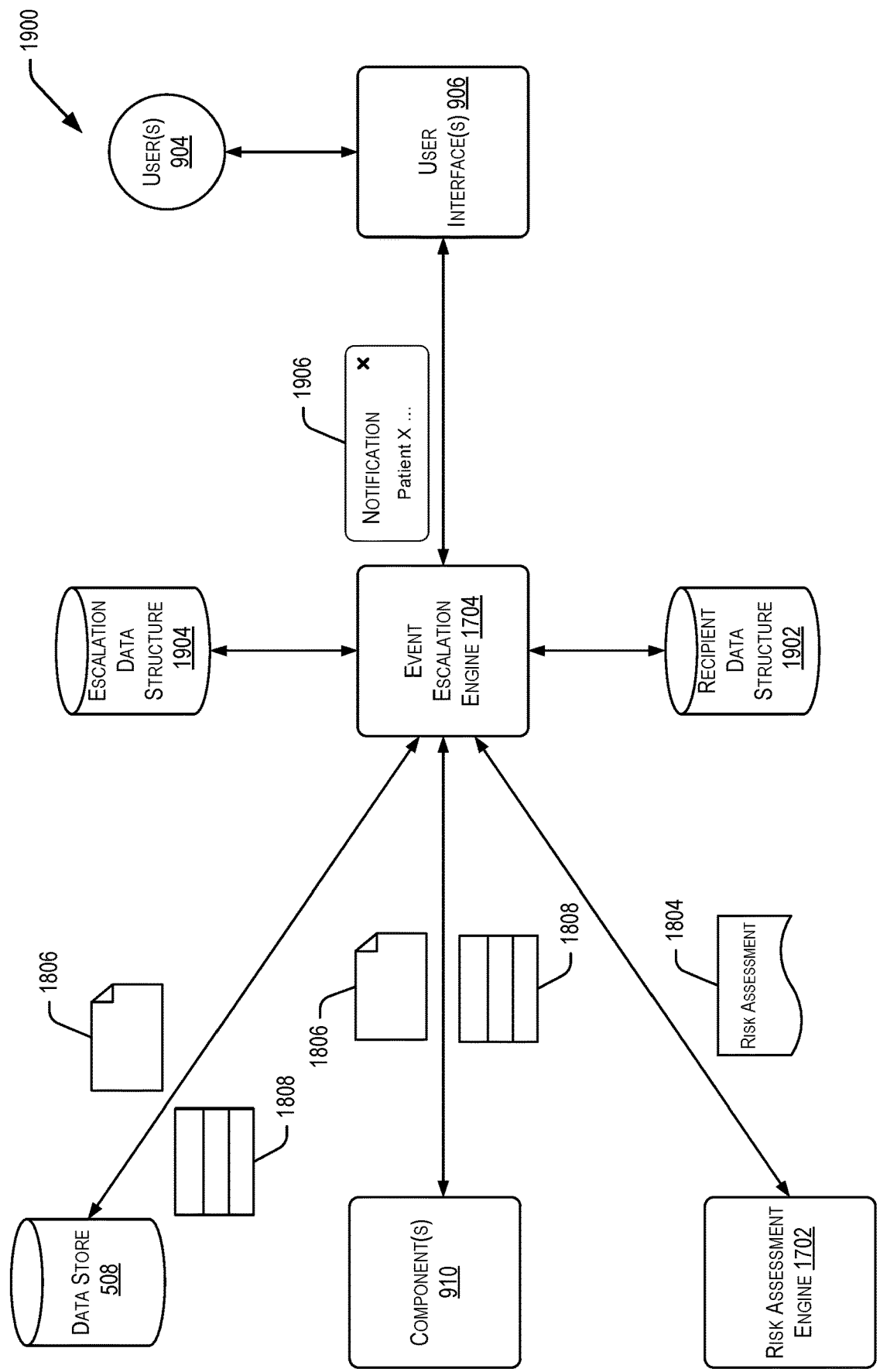
FIG. 19 is an example block diagram illustrating techniques relating to providing notifications to authorized users as described herein, according to at least one example.

Turning now to FIG. 19, a medical provider network 1900 is shown in accordance with an embodiment of the invention. The medical provider network 1900 includes the event escalation engine 1704 in communication with the data store 508 (associated with the transformative processing engine 202), the components 910, the user interfaces 906, the risk assessment engine 1702, a recipient data structure 1902, and an escalation data structure 1904. In some examples, the data store 508 and the risk assessment engine 1702 have the same characteristics in the medical provider network 1900 as they do in other medical provider networks described herein. Thus, the event escalation engine 1704, like the risk assessment engine 1702, accesses the unstructured data 1806 and/or the structured data 1808 from the data store 508 and/or from the components 910. Thus, in some examples, portions of the unstructured data 1806 and/or portions of the structured data 1808 are received in real-time from the components 910 that generated and/or aggregated the unstructured data 1806 and/or the structured data 1808. In some examples, this may enable the event escalation engine 1704 to receive medical-related data in real-time (e.g., at the network speed it takes for data to transfer from a component to the event escalation engine 1702). However, instead of using the unstructured data 1806 and/or the structured data 1808 to generate the risk assessment 1804, the event escalation engine 1704 uses the unstructured data 1806 and/or the structured data 1808 to identify the occurrence of a triggering event. A triggering event is a medical event that, once identified by the event escalation engine 1704, causes the event escalation engine 1704 to generate a notification 1906 to provide to the receiving users 904 via the user interfaces 906.

To this end, the event escalation engine 1704 is configured, at a high level, to monitor medical-related data (e.g., the unstructured data 1806 and/or the structured data 1808) that flows in and out of the data store 508 and/or from the components 910, to identify the occurrence of a particular medical event, to generate a notification, to determine an order of recipients according to which the notification will be provided, and to provide the notification to a first recipient of the order.

In some examples, the event escalation engine 1704 includes a list of possible medical events, with each possible medical event associated with one or more triggering rules. The list of possible medical events and associated triggering rules may be stored within the event escalation engine 1704 and/or within a data structure separate from the event escalation engine 1704. Each of the triggering rules defines one or more conditions that are to be fulfilled in order to trigger the triggering rule. In some examples, when a single triggering rule is triggered, the event escalation engine 1704 detects occurrence of the possible medical event associated with the single triggering rule. In some examples, to detect occurrence of the possible medical event by the event escalation engine 1704, more than one triggering rule must be triggered. Thus, similar to the symptom rules discussed herein, each triggering rule may be a necessary condition or a sufficient condition to detection of occurrence of a possible medical event.

After one or more triggering rules are triggered, the event escalation engine 1704 determines that a medical event has occurred. Because the event escalation engine 1704 is in communication with the recipient data structure 1902, the event escalation engine 1704 can determine to whom the event escalation engine 1704 should possibly send the notification 1906. To this end, the recipient data structure 1902 includes a directory of possible recipients. The directory of possible recipients identifies, for example, a name of the recipient, a title of the recipient, one or more addresses (device IP address, email address, etc.) for contacting the recipient, method for integrating the notification 1906 into an existing workflow associated with the recipient, relationships between recipients, and the like. Possible recipients include, for example, humans (e.g., doctors, nurses, policy makers, medical organization administrators, clinical trial administrators, patients, family members of patients, and other possible human recipients) or systems (e.g., electronic health record system, the medical suggestion engine 902, nurses stations) interested in receiving the notification 1906.

Depending on the type of medical event that has occurred and the identified recipient, the event escalation engine 1704 generates the notification 1906. This includes, for example, determining substance of the notification 1906, tone of the notification 1906, and format of the notification 1906. Thus, the notification 1906 can be tailored to the recipient. For example, if the recipient is a patient, the tone of the notification 1906 may be different than if the recipient were a doctor.

In order to determine which recipient of the possible recipients the event escalation engine 1704 should send the notification 1906, the event escalation engine 1704 accesses the escalation data structure 1904. The escalation data structure 1904 includes an escalation tree. The escalation tree includes relationships between the possible recipients from the recipient data structure 1902. The event escalation engine 1704 includes rules for providing the notification 1906 to the recipients and for escalating the notification 1906 to other recipients based on the escalation tree. For example, if a particular doctor is identified as a first possible recipient of the notification 1906, the event escalation engine 1704 may access the escalation data structure 1904 to identify whom to contact (and how to contact them) in case the doctor is unavailable or does not respond within a fixed period of time. In some examples, the escalation can take place outside of the event escalation engine 1704. For example, if the doctor is unresponsive, a nurse monitoring the doctor's "in box" of notifications, can escalate the notification 1906. In some examples, the nurse is identified by the event escalation engine 1704 as a second possible recipient and the notification 1906 is provided directly to the nurse in accordance with the escalation data structure 1904.

The event escalation engine 1704 includes the functionality to reconcile delivery of the notification 1906. In some examples, this functionality is used to determine whether the notification 1906 should be escalated to a different recipient.

Providing the notification 1906 to the user interfaces 906 may include providing the notification 1906 into existing workflows of the medical provider network 1900. For example, a patient may receive the notification 1906 at an inbox of an online patient portal. In another example, a doctor may receive the notification 1906 at an inbox of a medical practice management portal. In some examples, the user interfaces 906 represent one or more subscribing systems. In this example, the event escalation engine 1704 functions as a publisher and pushes certain information to the subscribing systems when information relevant to the subscribing systems is received. In this example, the event escalation engine 1704 may function as a messaging hub that receives medical-related information, and publishes messages, including a portion of the medical-related information, to subscribing systems when certain medical-related information triggers that the event escalation engine 1704 do so.

Figure 20:
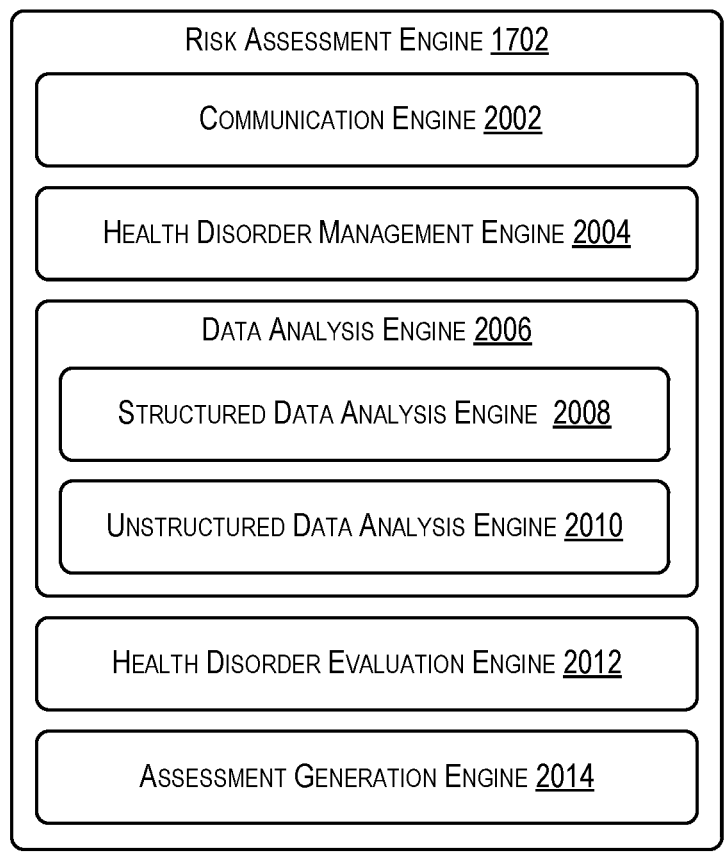
FIG. 20 is an example block diagram illustrating a risk assessment engine including a plurality of sub-engines for implemented techniques described herein, according to at least one example.

FIG. 20 illustrates aspects of the risk assessment engine 1702 in more detail in accordance with an embodiment of the invention. The risk assessment engine 1702 is configured to manage one or more sub-modules, components, engines, and/or services directed to examples disclosed herein. In some examples, the risk assessment engine 1702 includes a communication engine 2002, a health disorder management engine 2004, a data analysis engine 2006 (including a structured data analysis engine 2008 and an unstructured data analysis engine 2010), a health disorder evaluation engine 2012, and an assessment generation engine 2014. While these engines are illustrated in FIG. 20 and will be described as performing discrete tasks with reference to the flow charts, it is understood that FIG. 20 illustrates example configurations and other configurations performing other tasks and/or similar tasks as those described herein may be implemented according to the techniques described herein.

The communication engine 2002 is configured to enable communication with other elements of the medical provider networks described herein (e.g., the medical suggestion engine 902, the transformative processing engine 202, the event escalation engine 1704, etc). In some examples, the communication engine 2002 enables communication between other engines of the risk assessment engine 1702. The communication engine 2002 is also configured to enable communication with one or more components and one or more users. Thus, if a risk assessment is generated, the communication engine 2002 determines to whom to send the risk assessment and provides for its transport.

The health disorder management engine 2004 is configured to manage the lists of health disorders, symptoms associated with the health disorders, and the symptom rules associated with the symptoms. For example, an operator may add a new health disorder, symptoms, and rules using the health disorder management engine 2004.

The data analysis engine 2006 is configured to monitor, collect, receive, and evaluate medical-related data such that a risk assessment for a patient can later be generated. In particular, the structured data analysis engine 2008 is configured to monitor, collect, receive, and evaluate medical-related data that is in a structured format. This may include data that is objective in nature and which the structured data analysis engine 2008 anticipates receiving. The unstructured data analysis engine 2010 is configured to monitor, collect, receive, and evaluate medical-related data that is in an unstructured format. This may include data that is subjective in nature. To this end, as described herein, the unstructured data analysis engine 2010 executes one or more techniques to identify elements (e.g., letters, symbols, numbers, verbs, adjectives, nouns, punctuation, and other parts of speech) of spoken text and/or written text and characteristics of the spoken text and/or written text that may be relevant to their message (e.g., tone, meaning, sarcasm, feelings, inferences, impressions, attitude, outlook, positive/negative/other, and any other characteristic). These techniques include, for example, natural language processing (NLP) using machine learning, Hidden Markov models, Dynamic time warping (DTW), neural networks, deep neural networks and other deep learning models, and any other suitable technique for identifying elements and/or characteristics of spoken text and/or written text.

The health disorder evaluation engine 2012 is configured to evaluate the medical-related data analyzed by the data analysis engine 2006 and determine whether a particular health disorder is present. For example, in order to determine whether a particular symptom (of the health disorder) is present, the health disorder evaluation engine 2012 evaluates medical-related data to see if a symptom rule associated with the symptom is fulfilled by the medical-related data. Thus, the health disorder evaluation engine 2012 evaluates the symptom rules to determine, not only whether the associated symptoms are present, but also to determine whether a suitable number of symptoms (or score of one or more symptoms) are present to indicate that the associated health disorder is present.

The assessment generation engine 2014 is configured to generate risk assessments based on the results of the health disorder evaluation engine 2012. For example, if the health disorder evaluation engine 2012 determines that symptoms X, Y, and Z are present, and as a result, that health disorder A is 75% likely, the assessment generation engine 2014 can generate a risk assessment that includes this information. In some examples, the risk assessment includes a diagnosis of a particular health disorder.

Figure 21:
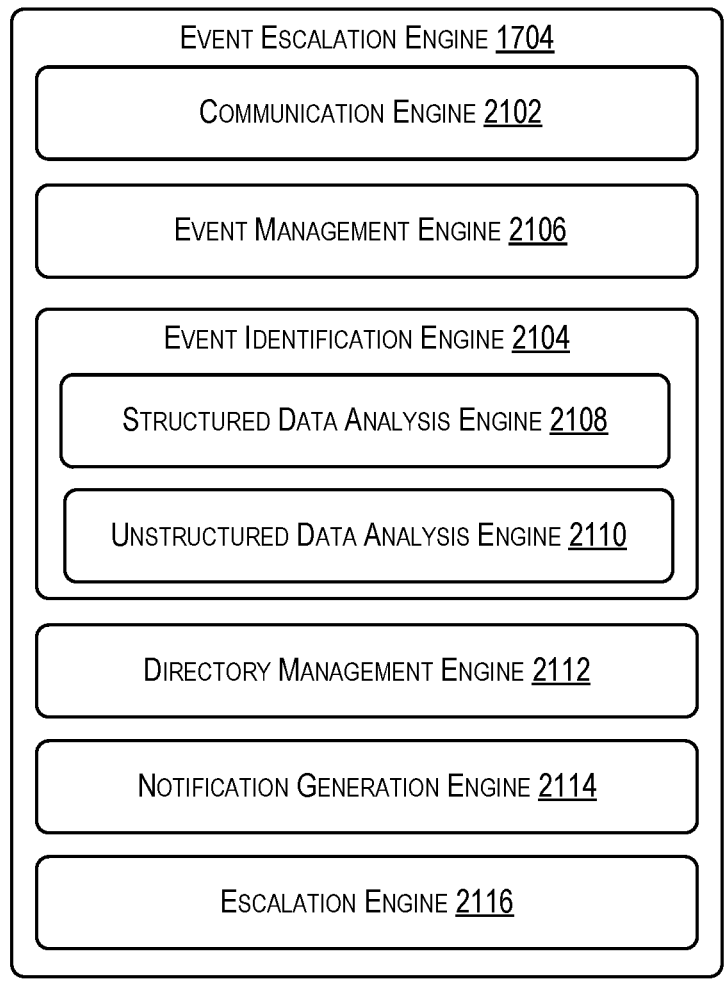
FIG. 21 is an example block diagram illustrating an event escalation engine including a plurality of sub-engines for implemented techniques described herein, according to at least one example.

FIG. 21 illustrates aspects of the event escalation engine 1704 in more detail in accordance with an embodiment of the invention. The event escalation engine 1704 is configured to manage one or more sub-modules, components, engines, and/or services directed to examples disclosed herein. In some examples, the event escalation engine 1704 includes a communication engine 2102, an event management engine 210, an event identification engine 2104 (including a structured data analysis engine 2108 and an unstructured data analysis engine 2110), a directory management engine 2112, a notification generation engine 2114, and an escalation engine 2116. While these engines are illustrated in FIG. 21 and will be described as performing discrete tasks with reference to the flow charts, it is understood that FIG. 21 illustrates example configurations and other configurations performing other tasks and/or similar tasks as those described herein may be implemented according to the techniques described herein.

The communication engine 2102 is configured to enable communication with other elements of the medical provider networks described herein (e.g., the medical suggestion engine 902, the transformative processing engine 202, the risk assessment engine 1702, etc). In some examples, the communication engine 2102 enables communication between other engines of the event escalation engine 1704. The communication engine 2102 is also configured to enable communication with one or more components and one or more users. Thus, if occurrence of an event is identified and a notification is generated, the communication engine 2102 determines whom to send the notification.

The event management engine 2106 is configured to access and manage the lists of possible events and triggering rules for detecting occurrence of the possible events. For example, an operator may add a new possible event and associated triggering rule(s) using the event management engine 2106.

The event identification engine 2104 is configured to monitor, collect, receive, and evaluate medical-related data. In particular, the event identification engine 2104 includes the structured data analysis engine 2108 and the unstructured data analysis engine 2110. The structured data analysis engine 2108 is configured to monitor, collect, receive, and evaluate medical-related data that is in a structured format. This may include data that is objective in nature and which the structured data analysis engine 2108 anticipates receiving. The unstructured data analysis engine 2110 is configured to monitor, collect, receive, and evaluate medical-related data that is in an unstructured format. This may include data that is subjective in nature. To this end, as described herein, the unstructured data analysis engine 2110 executes one or more techniques to identify elements (e.g., letters, symbols, numbers, verbs, adjectives, nouns, punctuation, and other parts of speech) of spoken text and/or written text and characteristics of the spoken text and/or written text that may be relevant to their message (e.g., tone, meaning, sarcasm, feelings, inferences, impressions, attitude, outlook, positive/negative/other, and any other characteristic). These techniques include, for example, natural language processing (NLP) using machine learning, Hidden Markov models, Dynamic time warping (DTW), neural networks, deep neural networks and other deep learning models, and any other suitable technique for identifying elements and/or characteristics of spoken text and/or written text.

The directory management engine 2112 is configured to manage and access one or more recipient data structures. As described herein, the one or more recipient data structures may include lists of recipients and suitable contact information for the recipients. In some examples, the directory management engine 2112 accesses the one or more recipient data structures in order to implement the techniques described herein.

The notification generation engine 2114 is configured to generate one or more notifications. For example, after the event identification engine 2104 has identified the occurrence of an event, the notification generation engine 2114 generates a notification. The notification, in some examples, is customized to a recipient and can include personal health information. In some examples, the notification indicates the event, which rules were triggered to detect occurrence of the event, a patient associated with the event, and any other suitable information pertaining to the event.

The escalation engine 2116 is configured to manage and access one or more escalation data structures. For example, after the event identification engine 2104 has identified the occurrence of an event, the escalation engine 2116 determines to whom a notification should be sent and also determines what steps should take place if the recipient is unresponsive or unable to respond to the notification.

Figure 22:
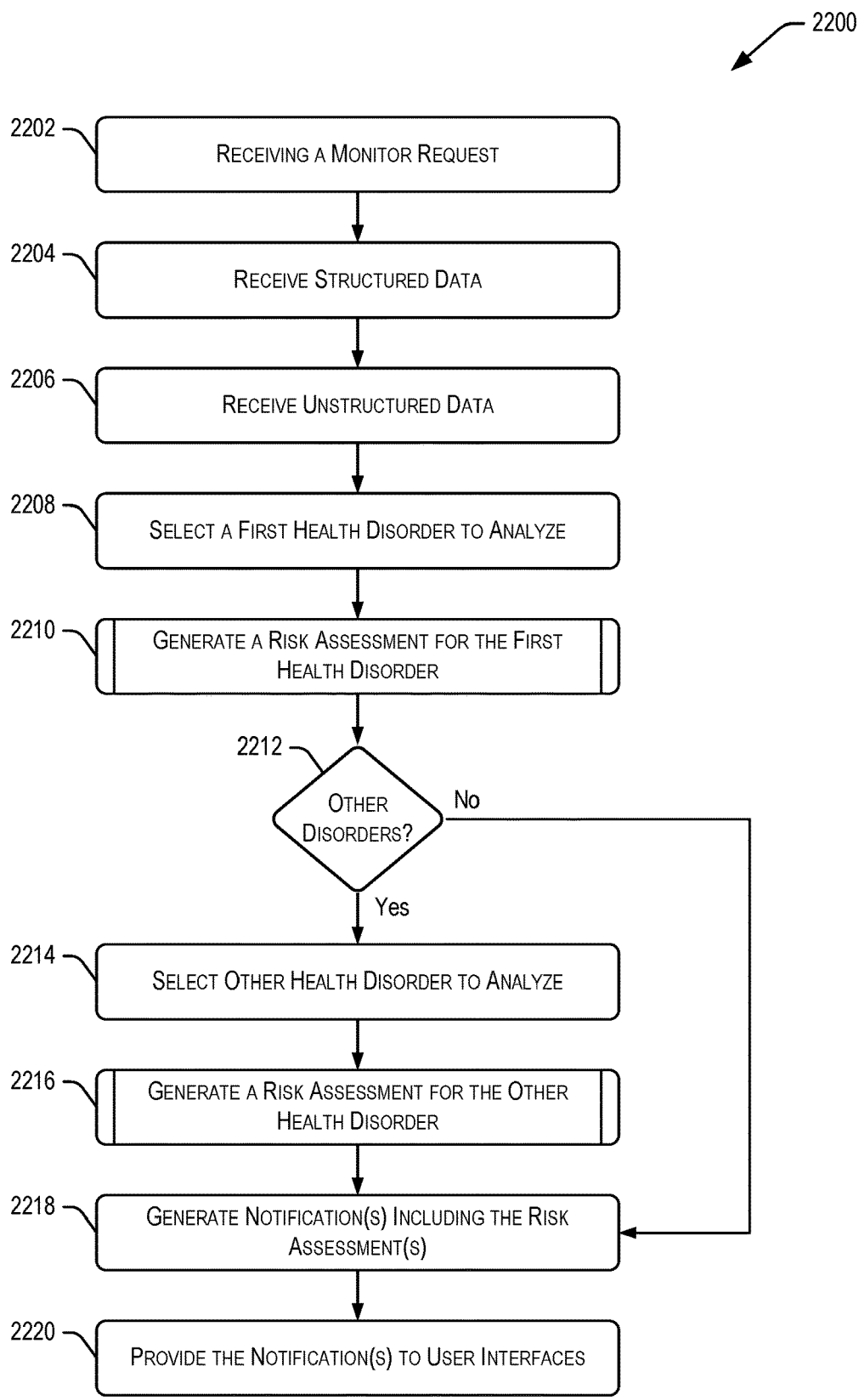
FIG. 22 is a flow diagram depicting example acts for implementing techniques relating to evaluating risk and generating a risk assessment for authorized users as described herein, according to at least one example.

FIG. 22 illustrates a flowchart of a process 2200 for generating a risk assessment according to an embodiment of the invention. Some or all of the process 2200 (or any other processes described herein, or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The process 2200 may be performed by the risk assessment engine 1702 (FIG. 20). The process 2200 begins at block 2202 by receiving a monitor request. This may be performed by the communication engine 2002 (FIG. 20). The monitor request may come from a patient or medical care professional or other individual and may indicate that a patient be monitored. For example, all patients in a particular wing of a hospital, patients who are admitted in post operation, certain high-risk patients, children, and others may be good candidates for monitoring.

At 2204, the process 2200 receives structured data. In some examples, this may be performed by the structured data analysis engine 2008 (FIG. 20). Receiving the structured data may include accessing the data in a data store. The structured data may include data which is in standard format. In some examples, the structured data may include Health Level 7 messages or other messages according to other comparable standardized message protocol.

At 2206, the process 2200 receives unstructured data. In some examples, this may be performed by the unstructured data analysis engine 2010 (FIG. 20). Receiving the unstructured data may include accessing the data in a data store. The unstructured data may be data that is not structured data.

At 2208, the process 2200 selects a first health disorder to analyze. In some examples, this may be performed by the health disorder evaluation engine 2012 (FIG. 20). Selecting the first health disorder may include selecting the first health disorder from a list of possible health disorders. In some examples, the list of possible health disorders is specific to a patient. In other words, there may be a list of all possible health disorders, which may be reduced to the list of possible health disorders relevant to the patient.

At 2210, the process 2200 generates a risk assessment for the first health disorder. In some examples, this may be performed by the risk assessment engine 1702 (FIG. 20). Generating the risk assessment at 2210 may include a sub-process discussed with reference to FIG. 23.

At 2212, the process 2200 determines whether there are other health disorders to analyze. In some examples, this may be performed by the health disorder evaluation engine 2012. This determination may include analyzing the list of possible medical conditions to identify other medical conditions to be analyzed. In some examples, depending on the risk assessment, other medical conditions may be identified as relevant to the patient, and that should be analyzed. For example, if the risk assessment identifies that the patient is at risk for disease X, the process 2200 may determine patients who have disease X also often have diseases Y and Z. Based on this, the process 2200 may determine that other health disorders (e.g., diseases Y and Z) should be evaluated.

If the answer at 2212 is NO, the process 2200 proceeds to 2218 where the process 2200 generates a notification including the risk assessment generated at 2210. In some examples, this may be performed by the assessment generation engine 2014, the event escalation engine 1704, and/or the medical suggestion engine 902.

If the answer at 2212 is YES, the process 2200 proceeds to 2214 where the process 2200 selects other health disorders to analyze. In some examples, block 2214 may function similar to block 2208, except that at 2214 the process is selecting other health disorders to analyze. In this manner, the process 2200 can select other health disorders that should be evaluated.

At 2216, the process 2200 generates a risk assessment for the other health disorder. In some examples, this may be performed by the risk assessment engine 1702. In some examples, generating the risk assessment at 2216 may be similar to 2210 and include a sub-process discussed with reference to FIG. 23.

At 2218, the process 2200 generates notifications including the risk assessment(s). The notification may include the risk assessment(s) generated at 2210 and any other risk assessments generated at 2216. In this manner, the notification may include all risk assessments generated for the patient. In some examples, a particular notification may be generated for each health disorder and corresponding risk assessment.

At 2220, the process 2200 provides the notification(s) to user interfaces. In some examples, this may be performed by the communication engine 2002. Providing the notification(s) may include sending the notifications directly to user devices or messaging systems, either of which may be sent as part of an existing workflow. In other words, the notifications may be provided to a customary location where medical care professionals typically receive notifications.

Figure 23:
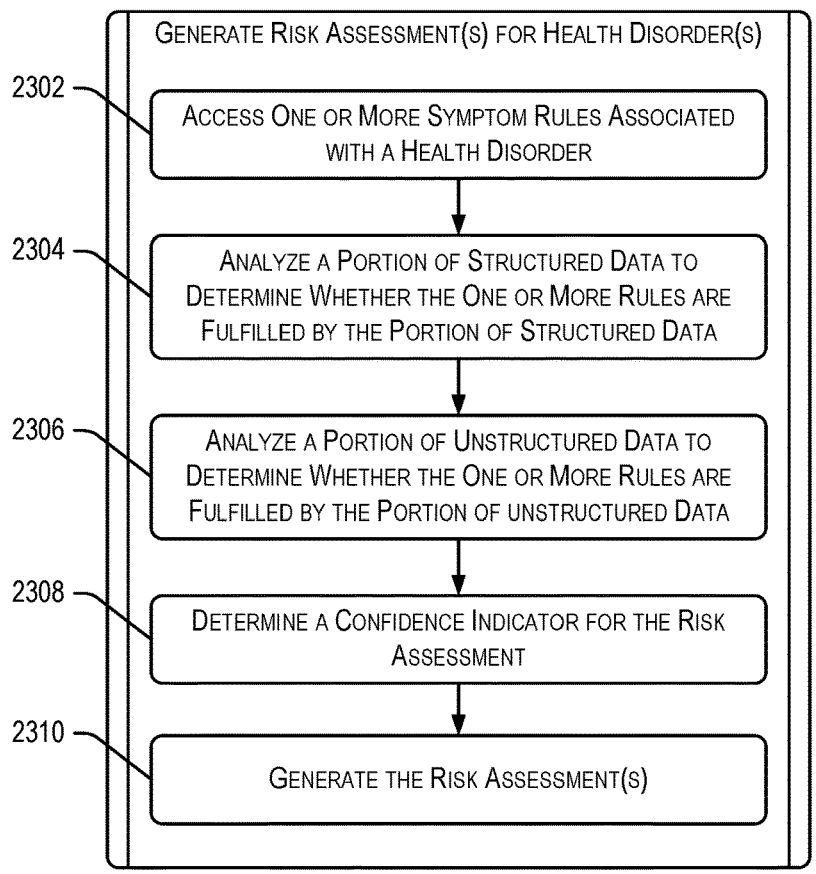
FIG. 23 is a flow diagram depicting example acts for implementing techniques relating to evaluating risk and generating a risk assessment for authorized users as described herein, according to at least one example.

FIG. 23 illustrates a flowchart of a sub-process 2300 for generating a risk assessment according to an embodiment of the invention. In some examples, the sub-process 2300 may correspond to blocks 2210 and 2216 of the process 2200. The sub-process 2300 begins at 2302 by accessing one or more symptom rules associated with a health disorder. In some examples, this may be performed by the health disorder evaluation engine 2012. Accessing the one or more symptom rules may include identifying the one or more symptom rules that may be included within the risk assessment engine 1702.

At 2304, the sub-process 2300 analyzes a portion of the structured data to determine whether the one or more rules are fulfilled by the portion of structured data. In some examples, this may be performed by the data analysis engine 2006 (FIG. 20) and/or the structured data analysis engine 2008 (FIG. 20). Analyzing the portion of the structured data may include analyzing the structured data to identify certain data that will fulfill conditions of the one or more rules. For example, for a certain health disorder, a first symptom rule may indicate that identification of a primary vital sign (e.g., body temperature, heart rate, respiratory rate, and blood pressure) that exceeds a fixed range, fulfills the condition of the first symptom rule. A second symptom rule may be more specific and indicate that identification of a lab result of blood glucose level falling outside a specific range fulfills the condition of the second symptom rule. In some examples, the symptom rules may be associated with each other. In this manner, the sub-process 2300 determines whether the symptom rules are fulfilled as they relate to other symptoms, instead of just in the abstract. This enables the sub-process 2300 (and the risk assessment engine 1702) to take a more holistic approach to generating the risk assessment.

At 2306, the sub-process 2300 analyzes a portion of the unstructured data to determine whether the one or more rule are fulfilled by the portion of unstructured data. In some examples, this may be performed by the data analysis engine 2006 and/or the unstructured data analysis engine 2010. In any event, analyzing the portion of the unstructured data may include using one or more language recognition techniques to identify whether the portion of unstructured data includes data that fulfills the symptom rules. For example, a first symptom rule may indicate that identification of "concern" in medical chart may fulfill the first symptom rule. The concern may be identified from notes entered in the medical chart of a nurse who watched over a patient overnight. It may be that the nurse could not "diagnose" the patient or identify anything particular wrong with the patient, but instead used terms, sentence structure, and the like in a manner that evidenced a concern for the patient. In some examples, a second symptom rule may indicate that identification that a patient is from or visited an geographical area may be enough to fulfill the second symptom rule. For example, a patient may have an undiagnosed case of Lyme disease. It may be unclear from the structured data that the patient has Lyme disease. However, in a conversation between the nurse and the patient, the patient may indicate that she recently returned from Connecticut where she visited her sister. Whether this is recorded in the nurse's note or in some other written text or recording (e.g., in the patient's room), at 2306, the sub-process 2300 may analyze the substance of that conversation and compare it with other unstructured and other structured data to determine its relevance. In this example, the identification of the visit to Connecticut coupled with other symptoms, may enable the system to generate a risk assessment for Lyme disease.

At 2308, the sub-process 2300 determines a confidence indicator for the risk assessment. In some examples, this may be performed by the assessment generation engine 2014 (FIG. 20). The confidence indicator may indicate how confident the system is that patient is at risk for the health disorder. In some examples, the confidence indicator may be derived from the number of symptom rules that were fulfilled, their relative weights, and any other suitable information. For example, if the patient has previously been admitted for a related health disorder, even if the symptom rules do not indicate this fact, the sub-process 2300 at 2308 may consider this information in determining the confidence indicator.

At 2310, the sub-process 2300 generates the risk assessment(s). This may be performed by the assessment generation engine 2014 as described herein.

Figure 24:
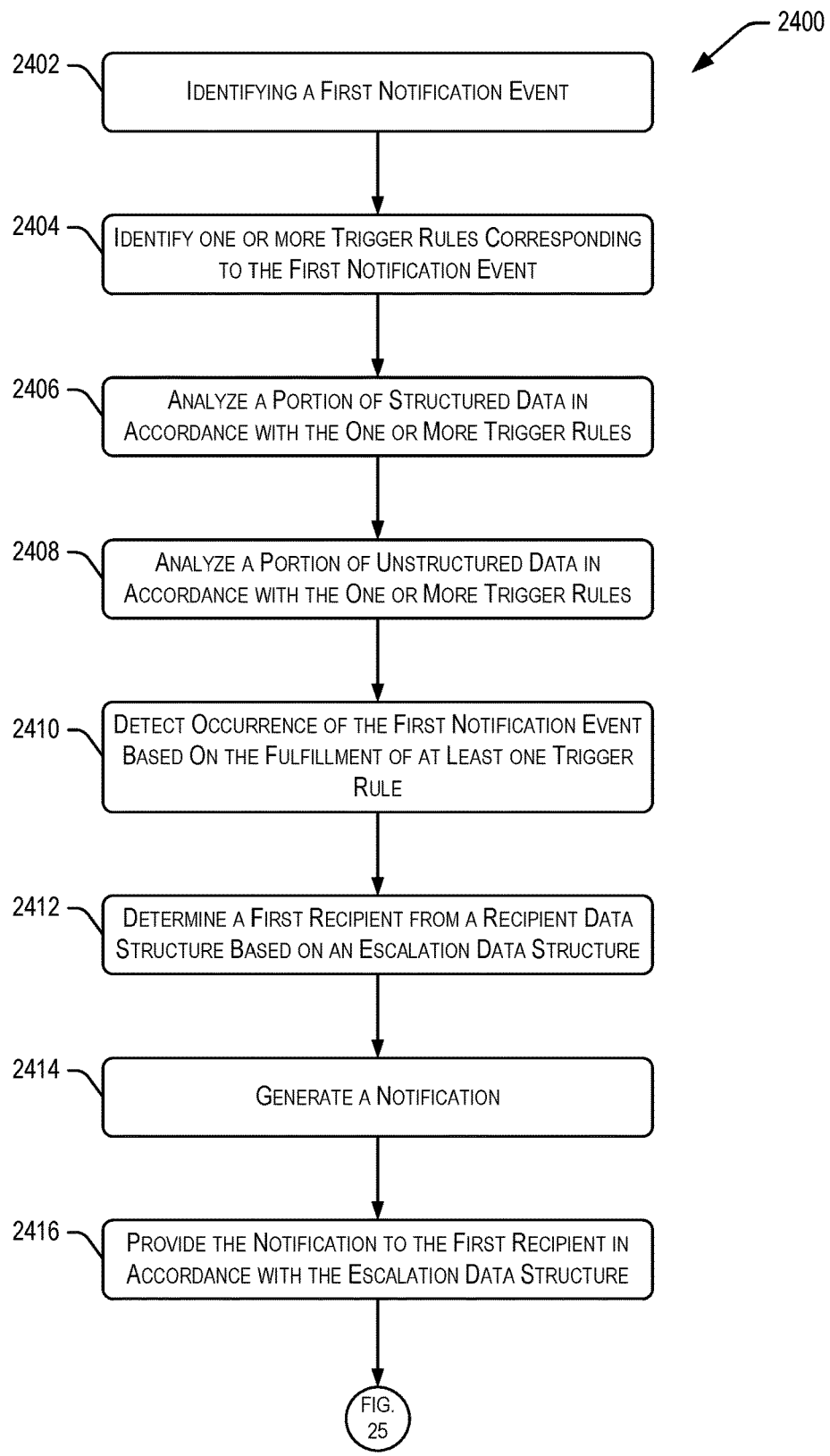
FIG. 24 is a flow diagram depicting example acts for implementing techniques relating to providing notifications to authorized users as described herein, according to at least one example.
Figure 25:
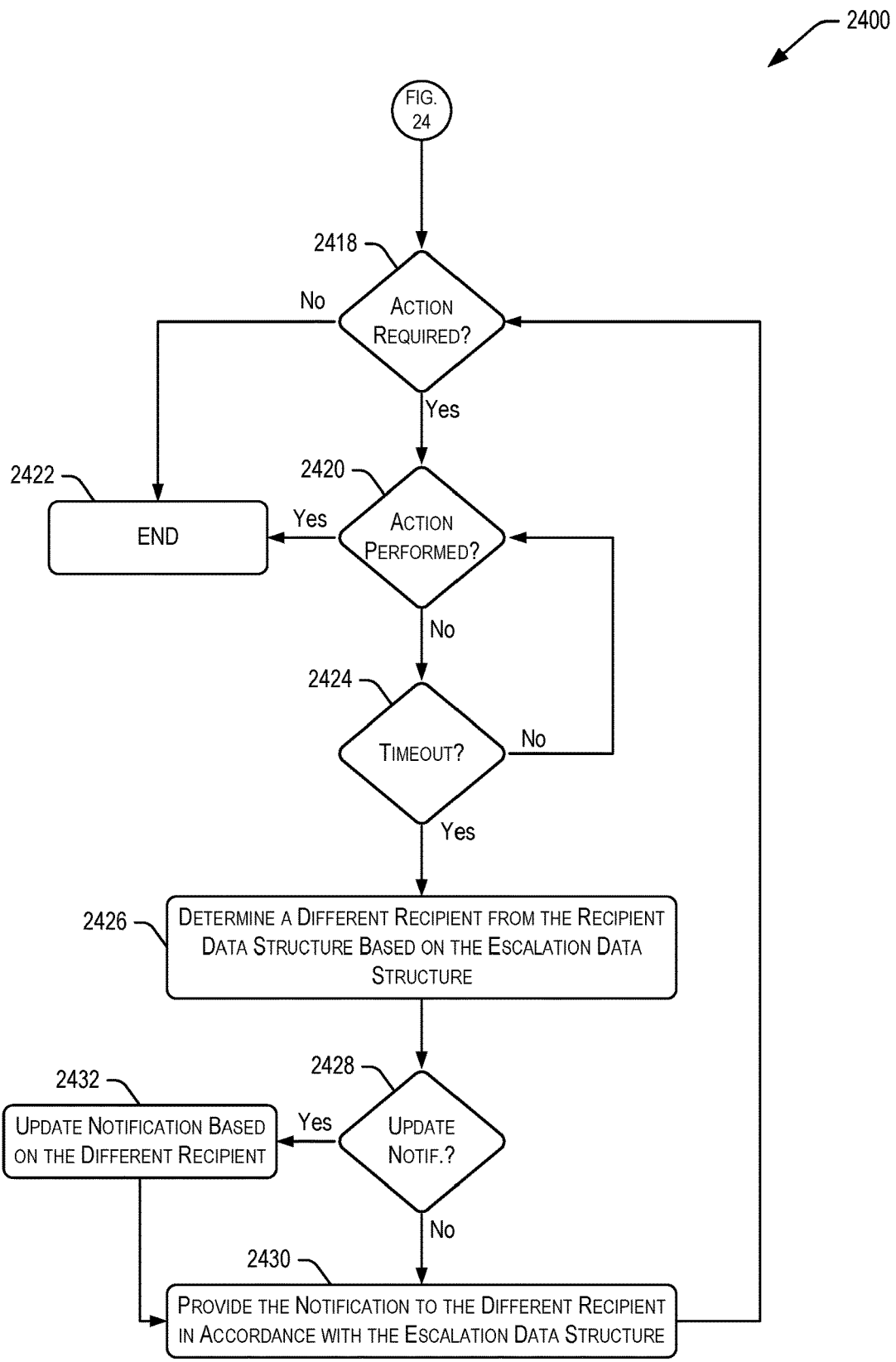
FIG. 25 is a flow diagram depicting example acts for implementing techniques relating to providing notifications to authorized users as described herein, according to at least one example.

FIGS. 24 and 25 illustrate flowcharts of process 2400 for providing notifications upon detection of an event according to an embodiment of the invention. The process 2400 may be performed by the event escalation engine 1704 (FIG. 21). The process 2400 begins at 2402 by identifying a first notification event. This may be performed by the event management engine 2106 (FIG. 21). For example, the first notification event may be included on a list of possible notification events. The list of possible notification events may be customized to a patient. Thus, the list of possible notification events may be shorter than a list of all events. In some examples, the list of possible notification events includes all or less than all events from the list of all events.

At 2404, the process 2400 identifies one or more triggering rules corresponding to the first notification event. In some examples, this may be performed by the event management engine 2106 (FIG. 21). For example, identifying the one or more triggering rules may include accessing the one or more triggering rules from memory of the event escalation engine 1704. In some examples, the one or more triggering rules may indicate that conditions under which detection of occurrence of the first notification event may be manifested.

At 2406, the process 2400 analyzes a portion of structured data in accordance with the one or more triggering rules. In some examples, this may be performed by the structured data analysis engine 2108 (FIG. 21). Analyzing the portion of structured data may include identifying data that is organized according to a known data structure and which triggers the one or more triggering rules. For example, a string of values may be interpreted by the process 2400 to identify what the string means and whether it fulfills a triggering rule. Such structured data, as described herein, may include results of certain tests, measurements of vital signs, prescriptions and other orders, and the like.

At 2408, the process 2400 analyzes a portion of unstructured data in accordance with the one or more triggering rules. In some examples, this may be performed by the unstructured data analysis engine 2110 (FIG. 21). Analyzing the portion of the unstructured data may include identifying data that is not organized according to a known data structure. This data may be in the form of prose, written text, and/or spoken text. This data can be analyzed to determine whether it fulfills a triggering rule.

At 2410, the process 2400 detects occurrence of the first notification event based on the fulfillment of at least one triggering rule. In some examples, this may be performed by the event identification engine 2104 (FIG. 21). Detecting occurrence of the first notification event may include identifying which triggering rules are fulfilled by the data analyzed at 2406 and 2408. Based on this, the occurrence of the first notification event can be detected.

At 2412, the process 2400 determines a first recipient from a recipient data structure based on an escalation data structure. In some examples, this may be performed by the directory management engine 2112 (FIG. 21). Determining the first recipient may depend at least in part on the event that was identified. For example, if the occurrence of the event was that a patient was moved from a first hospital room to a second hospital room, the first recipient may be caretaker of the patient, a family member, or a medical care professional. The detected event may also be something more subtle like identification of a large group visiting a patient, identification of an event requiring an administrative action, movement of a patient into a restricted area, an attempt to access restricted network services, and the like.

At 2414, the process 2400 generates a notification. In some examples, this may be performed by the notification generation engine 2114 (FIG. 21). Generating the notification may depend on the recipient and the event detected. In some examples, the notification may include a plan for resolving the event, which may be in the form of an instruction, suggestion, or request. In some examples, the notification may identify what rules were triggered to detect occurrence of the event, and any other suitable information to provide the first recipient context for the notification. In some examples, the tone and substance of the notification may depend on the first recipient and the event. In this manner, the notification may be tailored to the first recipient.

At 2416, the process 2400 provides the notification to the first recipient in accordance with the escalation data structure. In some examples, this may be performed by the communication engine 2102. Providing the notification in accordance with the escalation data structure may include identifying from the escalation data structure how to contact the first recipient. This may include providing the notification using existing systems and methods of providing notifications. In this manner, the notifications may become part of the first recipient's natural workflow. In some examples, providing the notification takes place on any communication layer service.

At 2418 (continued on FIG. 25), the process 2400 determines whether the notification requires action. In some examples, this may be performed by event management engine 2106. Determining whether the notification requires action may include determining whether the notification anticipates a response or the performance of some act. For example, a response may request that the recipient indicate that the notification was received. In some examples, the action includes a receiving system providing an indication to the sending system that the notification was received. In some examples, the notification indicates that the recipient of the notification perform one or more acts related to the notification. For example, the one or more acts may include reading or listening to the substance of the notification, interacting with the notification, sending the notification to other users, placing a lab order or writing a prescription, placing a phone call to another user, and any other suitable action.

If the answer at 2418 is NO, the process 2400 ends at 2422. If the answer at 2418 is YES, the process 2400 continues to 2420 where it is determined whether the action was performed. In some examples, this may be performed by the event management engine 2106. Determining whether the action was performed may include receiving feedback from the recipient and/or receiving system that the action from the notification was performed.

If the answer at 2420 is YES, the process 2400 ends at 2422. If the answer at 2420 is NO, the process 2400 continues to 2424 where it is determined whether the notification has timed out. In some examples, this may be performed by the event management engine 2106. This may include, for example, identifying whether a certain period of time has passed since the notification was sent and the current period. For example, a notification may indicate that a recipient perform a certain action within a predetermined time (e.g., 20 minutes) from when the notification was sent, or from when the notification was received. In any event, if an indication of the action being performed is not received by the sending system within the predetermined time, the notification may timeout. In this example, the answer at 2424 may be YES. If the answer at 2424 is NO, the process 2400 returns to 2420 where it is determined whether the action has been performed.

If the answer at 2424 is YES, the process 2400 proceeds to 2426 where the process 2400 determines a different recipient from the recipient data structure based on the escalation data structure. In some examples, this may be performed by the escalation engine 2116. Determining the different recipient may include accessing the escalation data structure to determine what action to take (e.g., to send to a different recipient, etc.). In some examples, the escalation data structure lists systems and/or individuals to contact when certain conditions are fulfilled.

At 2428, the process 2400 determines whether to update the notification. In some examples, this may be performed by the notification generation engine 2114. If the answer at 2428 is YES, the process 2400 proceeds to 2432 where the process 2400 updates the notification based on the different recipient. In some examples, this may be performed by the notification generation engine 2114. As the substance of the notification may depend on the recipient, when the different recipient is identified, the system may update the notification based on the different recipient. In this manner, the notification, while escalated to the different recipient, may nevertheless be tailored to the different recipient. In some examples, updating the notification may include updating the notification to include an increased urgency for the notification. This may be because the message has aged while waiting for the first recipient to receive the notification and/or perform the one or more actions indicated by the notification.

If the answer at 2428 is NO, the process 2400 proceeds to 2430 where the process 2400 provides the notification to the different recipient in accordance with the escalation data structure. In some examples, this may be performed by the communication engine 2102. Providing the notification in accordance with the escalation data structure may include identifying from the escalation data structure how to contact the different recipient. This may include providing the notification using existing systems and methods of providing notifications. In this manner, the notifications may become part of the different recipient's natural workflow. In some examples, providing the notification takes place on any communication layer service.

Figure 26:
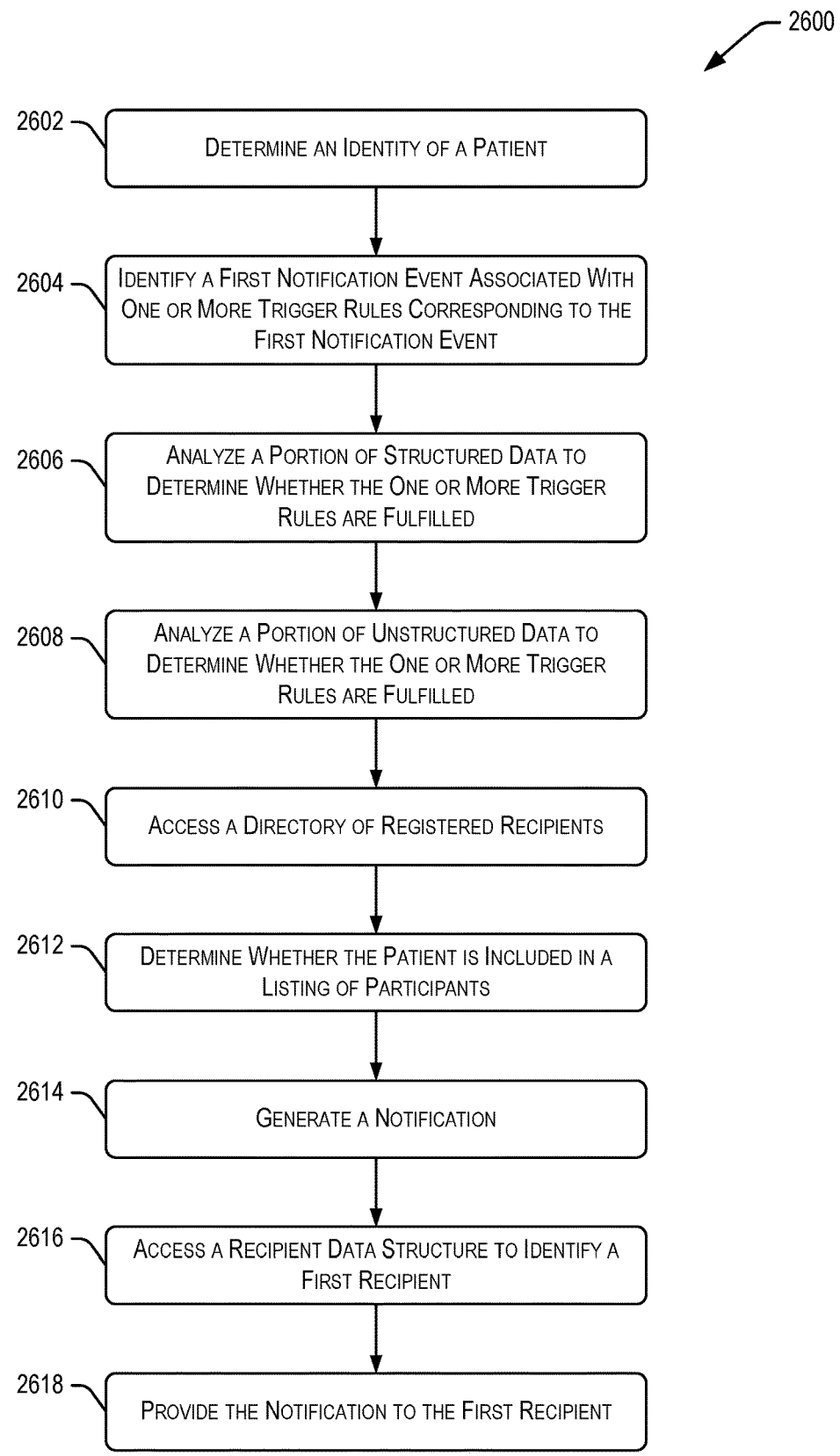
FIG. 26 is a flow diagram depicting example acts for implementing techniques relating to providing notifications to authorized users as described herein, according to at least one example.

FIG. 26 illustrates a flowchart of process 2600 for providing notifications to authorized users upon detection of an event according to an embodiment of the invention. The process 2600 may be performed by the event escalation engine 1704 (FIG. 21). The process 2600 begins at 2602 by determining an identity of a patient. Determining the identity of the patient may include receiving and/or accessing information indicating the identity. In some examples, a medical professional enters the identity of the patient into a computer system that is associated with the computer system which executes the process 2600.

At 2604, the process 2600 identifies a first notification event associated with one or more triggering rules corresponding to the first notification event. For example, identifying the first notification event may include accessing in memory a listing of possible notification events and their associated triggering rules. In some examples, the one or more triggering rules may indicate the conditions under which detection of occurrence of the first notification event may be manifested.

At 2606, the process 2600 analyzes a portion of structured data to determine whether the one or more triggering rules are fulfilled. Analyzing the portion of structured data may include identifying data that is organized according to a known data structure and which triggers the one or more triggering rules. For example, a string of values may be interpreted by the process 2600 to identify what the string means and whether it fulfills a triggering rule. Such structured data, as described herein, may include results of certain tests, measurements of vital signs, prescriptions and other orders, and the like. In some examples, the structured data may also include an indication that a patient has checked into hospital, has been seen at a clinic or emergency room, and the like.

At 2608, the process 2600 analyzes a portion of unstructured data to determine whether the one or more triggering rules are fulfilled. Analyzing the portion of the unstructured data may include identifying data that is not organized according to a known data structure. This data may be in the form of prose, written text, and/or spoken text. This data can be analyzed to determine whether it fulfills a triggering rule.

At 2610, the process 2600 accesses a directory of registered recipients. This may include recipients that have registered to receive notifications pertaining to patients associated with notification events. In some examples, the directory of registered recipients includes a list of administrators of clinical trials associated with patients. The directory may be a common directory that includes administrators and patients from a large number of ongoing, past, and future clinical trials.

At 2612, the process 2400 determines whether the patient is included in a listing of participants. In some examples, the listing of participants includes those participants, which may be the patient, who are participating in one or more ongoing, past, or future clinical trials.

At 2614, the process 2400 generates a notification. In some examples, the notification includes information describing the identity of the patient, the first notification event, which of the triggering rules were fulfilled to detect occurrence of the first notification event, and any other suitable information pertaining to the notification. For example, the notification may indicate that the patient is a participant in an ongoing clinical trial, visited an emergency room, and was treated by Dr. Wilson for dizziness.

At 2616, the process 2400 accesses a recipient data structure to identify a first recipient. In some examples, the recipient data structure is associated with the directory of registered recipients. In some examples, however, the recipient data structure may include information describing other possible recipients that are not also on the directory of registered recipients. For example, an administrator of a clinical trial may be in a directory of registered patients, while not in a recipient data structure. A friend of the patient's may be in the recipient data structure, but not in the directory of registered recipients. In any event, the process 2400 identifies the first recipient based on the recipient data structure. In some examples, the first recipient is identified based on the directory of registered recipients.

At 2618, the process 2400 provides the notification to the first recipient. Providing the notification may include identifying how to contact the first recipient. This may include providing the notification using existing systems and methods of providing notifications. In this manner, the notifications may become part of the first recipient's natural workflow. In some examples, providing the notification takes place on any communication layer service.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method, comprising:
generating a first contextual suggestion for a medical care professional that is tailored to at least:
a specialty specification mapped to the medical care professional; and
an electronic health record of a patient,
the first contextual suggestion corresponding to first content and a first set of one or more interface elements mapped to a first set of one or more medical tasks for presentation via a contextual interface;
identifying and specifying a first criticality level from a plurality of critical levels as corresponding to the first contextual suggestion;
causing transmission of an indication of the first contextual suggestion to a user device associated with the medical care professional to cause presentation corresponding to the first contextual suggestion, in accordance with a set of presentation rules, via the contextual interface, where:
the contextual interface comprises a plurality of presentation areas;
a first manner of presenting of the first contextual suggestion is selected from a plurality of presentation options based on the first criticality level identified as corresponding to the first contextual suggestion; and
the first manner of presenting of the first contextual suggestion comprises presenting the first contextual suggestion in a particular area of the plurality of presentation areas of the contextual interface;
generating a second contextual suggestion for the medical care professional that is tailored to at least:
tracking of one or more patterns of past treatment by the medical care professional;
the specialty specification mapped to the medical care professional; and
the electronic health record of the patient, the second contextual suggestion corresponding to a second set of one or more medical tasks;
the second contextual suggestion corresponding to second content and a second set of one or more interface elements mapped to the second set of one or more medical tasks for presentation via the contextual interface;
identifying and specifying a second criticality level from the plurality of critical levels as corresponding to the second contextual suggestion;
causing transmission of an indication of the second contextual suggestion to the user device associated with the medical care professional to cause presentation corresponding to the second contextual suggestion, in accordance with the set of presentation rules, via the contextual interface, where:
a second manner of presenting of the second contextual suggestion is selected from the plurality of presentation options based on the second criticality level identified as corresponding to the second contextual suggestion; and
the second manner of presenting of the second contextual suggestion comprises graphically differentiating the second contextual suggestion from the first contextual suggestion;
tracking performance of the medical care professional based at least in part on one or more actions of the medical care professional with respect to the second set of one or more medical tasks;
receiving medical analytics data from an aggregation engine of a medical network, the medical analytics data collected by the aggregation engine from at least one medical care facility comprising a plurality of medical components of the medical network, the medical analytics data corresponding to a plurality of medical care professionals comprising the medical care professional;
evaluating the medical analytics data with respect to a set of medical performance indicators associated with the medical care professional of the plurality of medical care professionals;
generating an updateable graphical representation that is representative of at least one medical performance indicator of the set of medical performance indicators based on evaluating the medical analytics data; and
providing the updateable graphical representation for presentation via the contextual interface of the user device.

2. The computer-implemented method of claim 1, further comprising, consequent to providing the updateable graphical representation for presentation via the contextual interface of the user device associated with the medical care professional:
receiving additional medical analytics data from the aggregation engine, the additional medical analytics data collected by the aggregation engine from the at least one medical care facility;
detecting a change to the at least one medical performance indicator based at least in part on the additional medical analytics data;
generating a changed updateable graphical representation based at least in part on detecting the change; and
providing the changed updateable graphical representation for presentation on the contextual interface of the user device.

3. The computer-implemented method of claim 2, wherein providing the updateable graphical representation for presentation on the contextual interface of the user device comprises providing the updateable graphical representation as a user interface element in a webpage.

4. The computer-implemented method of claim 3, wherein the webpage is customized for the medical care professional.

5. The computer-implemented method of claim 2, wherein:

the method further comprises receiving a selection of the at least one medical performance indicator; and wherein generating the updateable graphical representation comprises generating the updateable graphical representation based on the selection.

6. The computer-implemented method of claim 5, wherein receiving the selection of the at least one medical performance indicator comprises receiving the selection via a user input that selects a user interface element of the contextual interface.

7. The computer-implemented method of claim 1, wherein the updateable graphical representation comprises at least one of a table, a bar graph, or a pie chart.

8. The computer-implemented method of claim 1, wherein the aggregation engine is configured to perform data integration on raw data to create the medical analytics data.

9. A system, comprising:
a memory configured to store computer-executable instructions; and
a processor configured to access the memory and execute the computer-executable instructions to perform operations comprising:
generating a first contextual suggestion for a medical care professional that is tailored to at least:
a specialty specification mapped to the medical care professional; and
an electronic health record of a patient,
the first contextual suggestion corresponding to first content and a first set of one or more interface elements mapped to a first set of one or more medical tasks for presentation via a contextual interface;
identifying and specifying a first criticality level from a plurality of critical levels as corresponding to the first contextual suggestion;
causing transmission of an indication of the first contextual suggestion to a user device associated with the medical care professional to cause presentation corresponding to the first contextual suggestion, in accordance with a set of presentation rules, via the contextual interface, where:
the contextual interface comprises a plurality of presentation areas;
a first manner of presenting of the first contextual suggestion is selected from a plurality of presentation options based on the first criticality level identified as corresponding to the first contextual suggestion; and
the first manner of presenting of the first contextual suggestion comprises presenting the first contextual suggestion in a particular area of the plurality of presentation areas of the contextual interface;
determining a second contextual suggestion for the medical care professional that is tailored to at least:
tracking of one or more patterns of treatment by the medical care professional;
the specialty specification mapped to the medical care professional; and
the electronic health record of the patient, the second contextual suggestion corresponding to a second set of one or more medical tasks;
the second contextual suggestion corresponding to second content and a second set of one or more interface elements mapped to the second set of one or more medical tasks for presentation via the contextual interface;
identifying and specifying a second criticality level from the plurality of critical levels as corresponding to the second contextual suggestion;
causing transmission of an indication of the second contextual suggestion to the user device associated with the medical care professional to cause presentation corresponding to the second contextual suggestion, in accordance with the set of presentation rules, via the contextual interface, where:
a second manner of presenting of the second contextual suggestion is selected from the plurality of presentation options based on the second criticality level identified as corresponding to the second contextual suggestion; and
the second manner of presenting of the second contextual suggestion comprises graphically differentiating the second contextual suggestion from the first contextual suggestion;
tracking performance of the medical care professional based at least in part on one or more actions of the medical care professional with respect to the second set of one or more medical tasks;
receiving medical analytics data from an aggregation engine of a medical network, the medical analytics data collected by the aggregation engine from at least one medical care facility comprising a plurality of medical components of the medical network, the medical analytics data corresponding to a plurality of medical care professionals comprising the medical care professional;
evaluating the medical analytics data with respect to a set of medical performance indicators associated with the medical care professional of the plurality of medical care professionals;
generating an updateable graphical representation that is representative of at least one medical performance indicator of the set of medical performance indicators based on evaluating the medical analytics data; and
providing the updateable graphical representation for presentation via the contextual interface of the user device.

10. The system of claim 9, the operations further comprising, consequent to providing the updateable graphical representation for presentation via the contextual interface of the user device associated with the medical care professional:
receiving additional medical analytics data from the aggregation engine, the additional medical analytics data collected by the aggregation engine from the at least one medical care facility;
detecting a change to the at least one medical performance indicator based at least in part on the additional medical analytics data;
generating a changed updateable graphical representation based at least in part on detecting the change; and
providing the changed updateable graphical representation for presentation on the contextual interface of the user device.

11. The system of claim 10, wherein providing the updateable graphical representation for presentation on the contextual interface of the user device comprises providing the updateable graphical representation as a user interface element in a webpage.

12. The system of claim 11, wherein the webpage is customized for the medical care professional.

13. The system of claim 10, wherein:
the operations further comprise receiving a selection of the at least one medical performance indicator; and
wherein generating the updateable graphical representation comprises generating the updateable graphical representation based on the selection.

14. The system of claim 9, wherein the updateable graphical representation comprises at least one of a table, a bar graph, or a pie chart.

15. The system of claim 9, wherein the aggregation engine is configured to perform data integration on raw data to create the medical analytics data.

16. One or more non-transitory, computer-readable media comprising computer-executable instructions that, when executed by one or more computer systems, cause the one or more computer systems to perform operations comprising:
generating a first contextual suggestion for a medical care professional that is tailored to at least:
a specialty specification mapped to the medical care professional; and
an electronic health record of a patient,
the first contextual suggestion corresponding to first content and a first set of one or more interface elements mapped to a first set of one or more medical tasks for presentation via a contextual interface;
identifying and specifying a first criticality level from a plurality of critical levels as corresponding to the first contextual suggestion;
causing transmission of an indication of the first contextual suggestion to a user device associated with the medical care professional to cause presentation corresponding to the first contextual suggestion, in accordance with a set of presentation rules, via the contextual interface, where:
the contextual interface comprises a plurality of presentation areas;
a first manner of presenting of the first contextual suggestion is selected from a plurality of presentation options based on the first criticality level identified as corresponding to the first contextual suggestion; and
the first manner of presenting of the first contextual suggestion comprises presenting the first contextual suggestion in a particular area of the plurality of presentation areas of the contextual interface;
generating a second contextual suggestion for the medical care professional that is tailored to at least:
tracking of one or more patterns of treatment by the medical care professional;
the specialty specification mapped to the medical care professional; and
the electronic health record of the patient, the second contextual suggestion corresponding to a second set of one or more medical tasks;
the second contextual suggestion corresponding to second content and a second set of one or more interface elements mapped to the second set of one or more medical tasks for presentation via the contextual interface;
identifying and specifying a second criticality level from the plurality of critical levels as corresponding to the second contextual suggestion;
causing transmission of an indication of the second contextual suggestion to the user device associated with the medical care professional to cause presentation corresponding to the second contextual suggestion, in accordance with the set of presentation rules, via the contextual interface, where:
a second manner of presenting of the second contextual suggestion is selected from the plurality of presentation options based on the second criticality level identified as corresponding to the second contextual suggestion; and
the second manner of presenting of the second contextual suggestion comprises graphically differentiating the second contextual suggestion from the first contextual suggestion;
tracking performance of the medical care professional based at least in part on one or more actions of the medical care professional with respect to the second set of one or more medical tasks;
receiving medical analytics data from an aggregation engine of a medical network, the medical analytics data collected by the aggregation engine from at least one medical care facility comprising a plurality of medical components of the medical network, the medical analytics data corresponding to a plurality of medical care professionals comprising the medical care professional;
evaluating the medical analytics data with respect to a set of medical performance indicators associated with the medical care professional of the plurality of medical care professionals;
generating an updateable graphical representation that is representative of at least one medical performance indicator of the set of medical performance indicators based on evaluating the medical analytics data, the updateable graphical representation representing the medical analytics data for the plurality of medical care professionals; and
providing the updateable graphical representation for presentation via the contextual interface of the user device.

17. The one or more non-transitory, computer-readable media of claim 16, wherein providing the updateable graphical representation for presentation on the contextual interface of the user device comprises providing the updateable graphical representation as a user interface element in a webpage.

18. The one or more non-transitory, computer-readable media of claim 17, wherein the webpage is customized for the medical care professional.

19. The one or more non-transitory, computer-readable media of claim 16, wherein the operations further comprise:
receiving additional medical analytics data from the aggregation engine, the additional medical analytics data collected by the aggregation engine from the at least one medical care facility;
detecting a change to the at least one medical performance indicator based at least in part on the additional medical analytics data;
generating a changed updateable graphical representation based at least in part on detecting the change; and
providing the changed updateable graphical representation for presentation on the contextual interface of the user device.

20. The one or more non-transitory, computer-readable media of claim 16, wherein the second manner of presenting of the second contextual suggestion comprises presenting the second contextual suggestion in an area of the plurality of presentation areas of the contextual interface that is different from the particular area.

* * * * *